(12) United States Patent
Cooke et al.

(10) Patent No.: US 9,718,782 B2
(45) Date of Patent: Aug. 1, 2017

(54) TRKA KINASE INHIBITORS, COMPOSITIONS AND METHODS THEREOF

(71) Applicant: MERCK SHARP & DOHME CORP, Rahway, NJ (US)

(72) Inventors: Andrew J. Cooke, Doylestown, PA (US); Craig A. Stump, Pottstown, PA (US); Xu-Fang Zhang, Dresher, PA (US); Chun Sing Li, Shanghai (CN); Qinghua Mao, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/023,634

(22) PCT Filed: Sep. 17, 2014

(86) PCT No.: PCT/US2014/055979
§ 371 (c)(1),
(2) Date: Mar. 21, 2016

(87) PCT Pub. No.: WO2015/042088
PCT Pub. Date: Mar. 26, 2015

(65) Prior Publication Data
US 2016/0229804 A1    Aug. 11, 2016

(30) Foreign Application Priority Data

Sep. 22, 2013   (WO) ................ PCT/CN2013/083932

(51) Int. Cl.
| | | |
|---|---|---|
| *C07D 213/75* | (2006.01) | |
| *C07D 405/04* | (2006.01) | |
| *C07D 487/04* | (2006.01) | |
| *C07D 401/04* | (2006.01) | |
| *C07D 403/04* | (2006.01) | |
| *C07D 513/04* | (2006.01) | |

(Continued)

(52) U.S. Cl.
CPC .......... *C07D 213/75* (2013.01); *C07C 275/28* (2013.01); *C07D 231/40* (2013.01); *C07D 233/88* (2013.01); *C07D 239/42* (2013.01); *C07D 249/08* (2013.01); *C07D 257/04* (2013.01); *C07D 261/14* (2013.01); *C07D 263/32* (2013.01); *C07D 271/10* (2013.01); *C07D 277/44* (2013.01); *C07D 277/48* (2013.01); *C07D 285/12* (2013.01); *C07D 295/135* (2013.01); *C07D 311/88* (2013.01); *C07D 401/04* (2013.01); *C07D 403/04* (2013.01); *C07D 405/04* (2013.01); *C07D 405/12* (2013.01); *C07D 471/04* (2013.01); *C07D 487/04* (2013.01); *C07D 498/04* (2013.01); *C07D 513/04* (2013.01)

(58) Field of Classification Search
CPC .. C07D 213/75; C07D 231/40; C07D 233/88; C07D 401/04; C07D 403/04; C07D 239/42; C07D 249/08; C07D 471/04; C07D 261/14; C07D 277/44; C07D 513/04; C07D 257/04; C07D 263/32; C07D 271/10; C07D 277/48; C07D 285/12; C07D 295/135; C07D 405/04
See application file for complete search history.

(56) References Cited

U.S. PATENT DOCUMENTS

| | | | |
|---|---|---|---|
| 3,755,594 | A | 8/1973 | Adams et al. |
| 9,181,261 | B2 | 11/2015 | Stachel et al. |

(Continued)

FOREIGN PATENT DOCUMENTS

| | | |
|---|---|---|
| DE | 1948816 | 2/1970 |
| EP | 0761658 A1 | 3/1997 |

(Continued)

OTHER PUBLICATIONS

Registry RN893769-158-3-Entered STN: Jul. 17, 2006.

(Continued)

*Primary Examiner* — Irina Neagu
(74) *Attorney, Agent, or Firm* — Sylvia A. Ayler; John C. Todaro

(57) ABSTRACT

The present invention is directed to benzyl urea compounds of formula (I) which are tropomyosin-related kinase (Trk) family protein kinase inhibitors, and hence may be useful in the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor Trk-A, Trk-B and/or Trk-C.

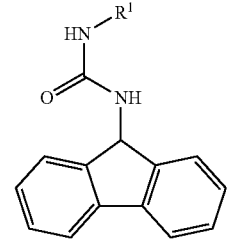

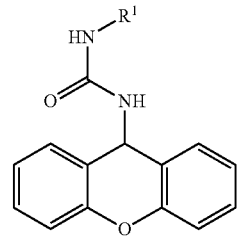

10 Claims, No Drawings

(51) Int. Cl.
| | |
|---|---|
| C07D 471/04 | (2006.01) |
| C07D 231/40 | (2006.01) |
| C07D 239/42 | (2006.01) |
| C07D 261/14 | (2006.01) |
| C07D 277/44 | (2006.01) |
| C07D 311/88 | (2006.01) |
| C07D 233/88 | (2006.01) |
| C07D 405/12 | (2006.01) |
| C07D 249/08 | (2006.01) |
| C07C 275/28 | (2006.01) |
| C07D 257/04 | (2006.01) |
| C07D 263/32 | (2006.01) |
| C07D 271/10 | (2006.01) |
| C07D 277/48 | (2006.01) |
| C07D 285/12 | (2006.01) |
| C07D 295/135 | (2006.01) |
| C07D 498/04 | (2006.01) |

(56) References Cited

U.S. PATENT DOCUMENTS

| | | |
|---|---|---|
| 2006/0270609 A1 | 11/2006 | Hammock et al. |
| 2008/0064688 A1 | 3/2008 | Flynn et al. |
| 2010/0105904 A1 | 4/2010 | Kimura et al. |
| 2010/0168182 A1 | 7/2010 | Mi et al. |
| 2010/0239526 A1* | 9/2010 | Ali ..................... C07D 471/04 424/85.4 |

FOREIGN PATENT DOCUMENTS

| | | |
|---|---|---|
| EP | 1181318 | 5/2000 |
| EP | 2019093 | 1/2009 |
| GB | 1181673 | 2/1970 |
| WO | WO0178698 | 10/2001 |
| WO | WO 03/051275 | * 6/2003 |
| WO | WO2004005184 | 7/2004 |
| WO | WO2004096122 | 11/2004 |
| WO | WO2005019266 | 3/2005 |
| WO | WO2005061540 | 7/2005 |
| WO | WO2005110994 | 11/2005 |
| WO | WO2006045119 | 4/2006 |
| WO | WO2006137106 | 6/2006 |
| WO | WO2006087538 | 8/2006 |
| WO | WO2006115452 | 11/2006 |
| WO | WO2006123113 | 11/2006 |
| WO | WO2006131952 | 12/2006 |
| WO | WO2007013673 | 2/2007 |
| WO | WO2007025540 | 3/2007 |
| WO | WO2008052734 | 5/2008 |
| WO | WO2010033941 | 3/2010 |
| WO | WO2010077680 | 7/2010 |
| WO | WO2012158413 | 11/2012 |

OTHER PUBLICATIONS

Assumi et al., Expression of Neurotrophins and Their Receptors (TRK) During Fracture Healing, Bone, 2000, pp. 625-633, 26.
Bardelli et al., Mutational Analysis of the Tryosine Kinome in Colorectal Cancers, Science, May 9, 2003, pp. 949, 300.
Brodeur et al., Neuroblastoma: Biological Insights into a Clincal Enigma, Nat. Rev Cancer, 2003, pp. 203-216, 3.
Dang et al., Expression of Nerve Growth Factor Receptors is Correlated with Progression and Prognosis of Human Pancreatic Cancer, J. of Gastroenterology and Hepatology, 2006, pp. 850-858, 21 (5).
Delafoy et al., Role of Nerve Growth Factor in the Trinitrobenzene Sulfonic Acid-Induced Colonic Hypersensitivity, Pain, 2003, pp. 489-497, 105.
Di Mola, Nerve Growth Factor and Trk Hihg Affinity Receptor (TRkA) Gene Expression in Inflammatory Bowel Disease, Gut, 2000, pp. 670-678, 46(5).
Dionne et al., Cell cycle-independent death of prostate adenocarcinoma is Induced by the trk Tyrosine Kinase Inhibitor CEP-751 (KT6587), Clinical Cancer Research, 1998, pp. 1887-1898, 4(8).
Dou et al., Increased nerve growth factor and its receptors in atopic dermatitis:, Archives of Dermatological Research, 2006, pp. 31-37 (1), 298.
Freund-Michel et al., The Nerve Growth Factor and Its Receptors in Airway Inflammatory Diseases, Pharmacology & Thereapeutics, 2008, pp. 52-76, 117 (1).
Hu et al., Decrease in Bladder Overactivity With REN1820 in Rats, J. of Urology, 2005, pp. 1016-1021, 173 (3).
Iannone, Increased Expression of Nerve Growth Factoer (NGF) and high Affinity NGF Receptor (p140 TrkA) in Human Osteoarthritic Chondrocytes, Rheumatology, 2002, pp. 1413-1418, 4.
Jaggar et al., Inflammation of the Rat Urinary Bladder is associated with a Referred Thermal Hyperalgesia Which is Nerve Growth Factor Dependent, Br. J. Anaesth., 1999, pp. 442-448, 83.
Kruettgen et al., The Dark Side of the NGF Family: Neurotrophin in Neoplasia, Brain Pathology, 2006, pp. 304-310, 16.
Lamb et al., Nerve Growth Factor and Gastric Hyperalgesia in the Rat, Neurogastroenterol Motil., 2003, pp. 355-361, 15.
Ma et al., The Progressive Tactile Hyperalgesia Induced by Peripheral Inflammation is Nerve Growth Factor Dependent, Neuroreport, 1997, pp. 807-810, 8.
Marchetti et al., Frequent Mutations in the Neuroptrophic Trrosine Receptor Kinase Gene Family in Large Cell Neuroendocrine Carcinioma of the Lung, Rapid Communication, 2008, pp. 609-616, 29 (5).
McMahon et al., The Biological Effects of Endogenous Nerve Growth Factor on Adult Sensory Neurons Revealed by a trkA-IgG Fusion Molecule, Nature Medicine, 1995, pp. 774-780, 1.
Raychaudhuri et al., K252a, a High-Affinity Nerve Growth Factor Receptor Blocker,, J. of Investigative Dermatology, 2004, pp. 812-819, 122 (3).
Registry-RN854654-64-1, Entered STN: Jul. 12, 2005.
Registry RN 36443489-48-9, Entered STN: Jul. 17, 2001.
Registry-RN1137154767, Entered STN: Apr. 20, 2009.
Registry-RN1177656-25-5, Entered STN: Aug. 30, 2009.
Registry-RN1422364939, Entered STN: Mar. 5, 2013.
Registry-RN26454228, , Entered STN, Nov. 16, 1984.
Registry-RN859739563, Entered STN: Aug. 11, 2005.
Registry-RN860571784, Entered STN: Aug. 17, 2005.
Registry-RN860574567-Entered STN: Apr. 20, 2009.
Registry-RN893764266-Entered STN: Jul. 17, 2006.
Registry-RN893777-66-7, Entered STN: Aug. 17, 2005.
Registry-RN893781583, Entered STN: Jul. 17, 2006.
RN860749957-Entered STN; Aug. 18, 2005.
Shelton et al., Nerve growth factor mediates hyperalgesia and cachexia, Pain, 2005, pp. 8-16, 116.
Sohrabji et al., Estrogen-BDNF interactions: Implications, Frontiers in Neuroendocrinology, 2006, pp. 404-414, 27(4).
Tripathy et al., TrkA kinase inhibitors from a library of modified and isosteric, Bioganic & Medicinal Chemistry Letters, 2008, pp. 3551-3555, 18.
Undevia et al., Phase I Clinical Trial of CEP-2563 Dihydrochloride, A Receptor Tyrosine Kinase Inhibitor, in Patients with Refractory Solid Tumors, Investigational New Drugs, 2004, pp. 449-458, 22.
Wang et al., Trk Kinase Inhibitors as New Treatments for Cancer and Pain, Expert Opinion, 2009, pp. 305-319, 19(3).
Winum et al., Ureido-Substituted Sulfamates Show Potent Carbonic Anhydrase IX Inhibitory and Antiproliferative Activities Against Breast Cancer Cell Lines, Bioorganic & Medicinal Chemistry Letters, Jul. 15, 2012, pp. 4681-4685, 15.
Woolf, Nerve Growth Factor Contributes to the Generation of Inflammatory Sensory Hypersenstivity, Neuroscience, 1994, pp. 327-331, 62.
Zhan et al., Effect of Blockade of Nerve Growth Factor and Tumor Necrosis Factor on Pain Behaviors After Plantar Incision, J. Pain, 2004, pp. 157-163, 5.

Zhu et al., Nerve Growth Factor Expression Correlation with Perineural Invasion and Pain in Human Pancreatic Cancer, J. of Clinicl Oncology, 1999, pp. 2419-2428, 17.

Registry-RN 893769-15-8, entered STN:Jul. 17, 2006 (Jul. 17, 2006).

Database Registry [Online] Chemical Abstracts Service, Columbus, Ohio, US; Jul. 17, 2001 (Jul. 17, 2001), XP002766146, Database Accession No. 346443-48-9.

Database Registry [Online] Chemical Abstracts Service, Columbus, Ohio, US; Jul. 17, 20016 (Jul. 17, 2006) XP002766146, Database Accession No. 893764-26-6.

Database Registry [Online] Chemical Abstracts Service, Columbus, Ohio, US; Jul. 17, 2006 (Jul. 17, 2006), XP002766149, Database Accession No. 893764-34-6.

Database Registry [Online] Chemical Abstracts Service, Columbus, Ohio, US; Jul. 17, 2006 (Jul. 17, 2006), XP002766150, Database Accession No. 893769-15-8.

Database Registry [Online] Chemical Abstracts Service, Columbus, Ohio, US; Jul. 17, 2006 (Jul. 17, 2006), XP002766151, Database Accession No. 893777-61-2.

Database Registry [Online] Chemical Abstracts Service, Columbus, Ohio, US; Jul. 17, 2006 (Jul. 17, 2006), XP002766167, Database Accession No. 893777-66-7.

Database Registry [Online] Chemical Abstracts Service, Columbus, Ohio, US; Jul. 17, 2006 (Jul. 17, 2006), XP002766168, Database Accession No. 893781-58-3.

Database Registry [Online] Chemical Abstracts Service, Columbus, Ohio, US; Mar. 17, 2004 (Mar. 17, 2004), XP002766147, Database Accession No. 663935-68-0.

Database Registry [Online] Chemical Abstracts Service, Columbus, Ohio, US; Aug. 30, 2009 (Aug. 30, 2009), XP002766169, Database Accession No. 1177656-25-5.

Harris et al., The Alkaline Hydrolysis of Fluorenonespiorhydantoin, J. of American Chemical Society, 1946, pp. 846-848 68.

Hirota et al., High-Performance Liquid Chromatographic Method for the Determination of Plasma Allantonin, J. of Chromatography B: Biomedical Sciences and Applications, 1983, pp. 165-172, 277.

M. W. Adriani, L'action du xanthydroi avec quelques Amides et Amines, Recueil Des Travaux Chimiques Des Pays-bas, Elsevier Science Publishers, 1916, pp. 180-210, 35.

Sawicki et al., Reaction of Thiaxanthydrol with Compounds Containing Active Hydrogen, J. of Organic Chemistry, 1956, pp. 183-189, 21.

\* cited by examiner

TRKA KINASE INHIBITORS, COMPOSITIONS AND METHODS THEREOF

CROSS REFERENCE TO RELATED APPLICATIONS

This application is the National Stage of International Application No. PCT/US2014/055979 filed on Sep. 17, 2014, which claims the benefit of International Patent Application No. PCT/CN2013/083932, filed Sep. 22, 2013.

FIELD OF THE INVENTION

The invention is directed to a class of substituted ureas, their salts, pharmaceutical compositions comprising them and their use in therapy of the human body. In particular, the invention is directed to a class of substituted ureas, which are tropomyosin-related kinase (Trk) family protein kinase inhibitors, and hence may be useful in the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA.

BACKGROUND OF THE INVENTION

Trk's are high affinity binding protein kinase receptors that are activated by Neurotrophins (NT), a group of soluble growth factors Nerve Growth Factor (NGF), Brain-Derived Neurotrophic Factor (BDNF) and Neurotrophin 3-5 (NT 3-5). The Trk's are made up of three family members TrkA, TrkB and TrkC that bind to and mediate the the signal transduction derived from the Neurotrophins. NGF activates TrkA, BDNF and NT-4/5 activate TrkB and NT3 activates TrkC.

Inhibitors of the Trk/neutrophin pathway have been demonstrated to be highly effective in numerous pre-clinical animal models of pain. Antagonistic NGF and TrkA antibodies have been shown to be efficacious in inflammatory and neuropathic pain animal models and in human clinical trials. See Woolf, C. J. et al. (1994) *Neuroscience* 62, 327-331; Zahn, P. K. et al. (2004) *J Pain* 5, 157-163; McMahon, S. B. et al., (1995) *Nat. Med.* 1, 774-780; Ma, Q. P. and Woolf, C. J. (1997) *Neuroreport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; and Jaggar, S. I. et al. (199) *Br. J Anaesth.* 83, 442-448. Through gene disruption studies in mice the TrkA-NGF interaction was found to be required for the survival of certain peripheral neuron populations involved in mediating pain signaling in the case of pancreatic cancer—an increase in the expression of TrkA was shown to correlate with an increase level of pain signaling (Zhu et al., *Journal of Clinical oncology*, 17:2419-2428 (1999)). Increased expression of NGF and TrkA was also observed in human osteoarthritis chondrocytes (Iannone et al, *Rheumatology* 41:1413-1418 (2002)). In particular, anti-TrkA antibodies and anti-NGF antibodies have been demonstrated to be effective analgesics in in vivo models of inflammatory and neuropathic pain. See WO2006/131952, WO2005/061540, EP1181318 and WO01/78698, WO2004/058184 and WO2005/019266, respectively. See also WO2004/096122 and WO2006/137106 which describe the use of an anti-TrkA antibodiy in combination with an opioid analgesic for the treatment or prevention of pain.

Trk inhibitors that can induce apotosis of proliferating osteoblast may be useful in treating diseases related to an imbalance of the regulation of bone remodeling, such as osteoporosis, rheumatoid arthritis and bone metastases. The expression of TrkA and TrkC receptors in the bone forming area in mouse models of bone facture and localization of NGF in almost all bone forming cells have been observed (K. Asaumi, et al., *Bone* (2000) 26(6) 625-633). See also *Exper Opin. Ther. Patents* (2009) 19(3)), WO2006/115452 and WO2006/087538, WO6123113, WO10033941, WO10077680, WO2005110994, Investigational New Drugs (2004), 22, 449-458 and R. Tripathy, et al., *Bioorganic & Medicinal Chem Ltrs.*, 2008, 18, 3551-3555. The association between overexpression, activation, amplification and/or mutation of Trks and several cancers as seen with studies conduct on neuroblastoma (Brodeur, G. M., *Nat. Rev. Cancer* 2003, 3, 203-216), ovarian cancer (Kruettgen et al., *Brain Pathology* 2006, 16: 304-310), prostate cancer (Dionne et al., *Clin. Cancer Res.* 1998, 4(8): 1887-1898), pancreatic cancer (Dang et al., *J of Gastroenterology and Hepatology* 2006, 21(5): 850-858), large cell neuroendocrine tumors (Marchetti et al., *Human Mutation* 2008, 29(5), 609-616, and colorectal cancer (Bardelli, A., *Science* 2003, 300, 949) support the reasoning that therapeutic implications of an effective Trk inhibitor may extend far beyond pain therapy. See also WO07013673, WO07025540, WO08052734, WO2012/158413 and U.S. Patent Application Ser. No. 61/650,019.

Also promising is the utility of Trk inhibitors in the treatment of inflammatory lung diseases such as asthma (Freund-Michel, V; et al., *Pharmacology & Therapeutics* (2008), 117(1), 52-76), interstitial cyctitis (Hu Vivian Y; et. al., *J of Urology* (2005, 173(3), 1016-21), inflammatory bowel disease including ulcerative colitis and Chron's disease (Di Mola, F. F., et al., *Gut* (2000), 46(5), 670-678 and inflammatory skin diseases such as atopic dermatitits (Dou, Y. C., et. Al., *Archives of Dermatological Research* (2006), 298(1), 31-37, eczema and psoriasis (Raychaudhuri, S. P. et. al., *J of Investigative Dermatology* (2004), 122(3), 812-819).

Modulation of the neutrophin/Trk pathway also has been shown to have an effect in the etiology neurodegenerative diseases including multiple sclerosis, Parkinson's disease and Alzheimer's disease (Sohrabji, et. al., *Neuroendocrinology* (2006), 27(4), 404-414).

Thus, the compounds of the invention, which are Trk inhibitors, may be useful in the treatment of multiple types of acute and chronic pain including but not limited to inflammatory pain, neuropathic pain, and pain associated with cancer, surgery and bone fracture. The compounds may also useful in the treatment of cancer, inflammation, neurodegenerative diseases and certain infectious diseases.

SUMMARY OF THE INVENTION

The present invention is directed to fluorine compounds of generic formula (I) below or pharmaceutically acceptable salts thereof that may be useful as a Trk kinase mediator of NGF driven biological responses.

The invention is further directed to methods of treating a patient for diseases or disorders in which the NGF receptor Trk kinases are involved, in particular TrkA. The invention further involves use of the compounds as NGF receptor TrkA, Trk B and/or Trk C inhibitor and/or antagonist for the preparation of a medicament for the treatment and/or prevention of diseases associated with inhibiting TrkA, Trk B and/or Trk C, which includes pain, cancer, restenosis, atherosclerosis, psoriasis, thrombosis, or a disease, disorder, or injury relating to dysmyelination or demyelination. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to compounds of general formula I or Ia

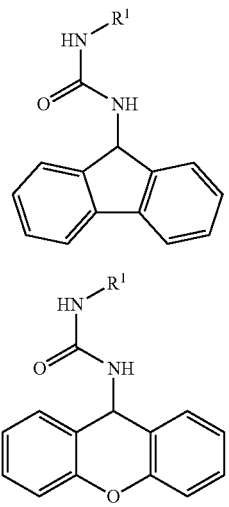

and pharmaceutically acceptable salts thereof, wherein:
R represents hydrogen, or $C_{1-6}$ alkyl;
$R^1$ is selected from $(CRR)_nC_{6-10}$ aryl, $C_{5-10}$ heterocycle, said aryl, and heterocycle optionally substituted with 1 to 3 groups of $R^a$;
$R^a$ represents —CN, —O—, —$(CH_2)_nC_{1-4}$haloalkyl, —$C_{1-6}$ alkyl, —$C_{1-6}$alkenyl, —$C_{1-6}$alkynyl, —$(CHR)_nC_{6-10}$ aryl, —$(CHR)_nC_{5-10}$ heterocycle, —$C_{3-10}$ cycloalkyl, —O—$(CH_2)_nC_{6-10}$ aryl, —O—$C_{5-10}$ heterocycle, —C(O)CF$_3$, —$(CH_2)_n$halo, —OR, —NRR, NHC$_{6-10}$aryl, —SCF$_3$, SO$_2$CF$_3$, OC(F)$_2$Cl, OC$_{1-4}$ haloalkyl, C(O)NRR, SO$_2$R, SO$_2$NRR, OC(F)$_2$C(F)$_3$, S(O)$_2$CH(F)$_2$, OC(F)$_2$CH(F)$_2$, C(CH$_3$)$_2$C≡N, —COC$_{6-10}$ aryl, or —CO$_2$R, said cycloalkyl, alkyl, aryl and heterocycle optionally substituted with 1 to 3 groups of $R^b$;
$R^b$ represents, —CN, —$(CH_2)_nC_{1-4}$haloalkyl, —OR, —$C_{1-6}$ alkyl, $(CH_2)_nOR$, —$(CHR)_nC_{6-10}$ aryl, —$(CHR)_nC_{5-10}$ heterocycle, —$C_{3-10}$ cycloalkyl, —$(CH_2)_n$halo, said aryl and heterocycle optionally substituted with 1 to 3 groups of $C_{1-6}$alkyl, or halo, and
n represents 0-6.

In an embodiment of this invention $R^1$ is optionally substituted $(CRR)_nC_{6-10}$ aryl and all other variables are as originally described. A subembodiment of this invention is realized when the n in $(CRR)_nC_{6-10}$ aryl is zero. Still another subembodiment of this invention is realized when $R^1$ is optionally substituted phenyl.

In another embodiment of the invention $R^1$ is phenyl substituted with optionally substituted phenyl, triazolyl, imidazoly, oxazolyl, tetrazolyl, oxadiazolyl, phenyl, thiadiazolyl, imidazolyl, pyrrolotriazolyl, piperazinyl, morpholinyl, or C(O)N(R)$_2$.

In another embodiment of this invention $R^1$ is optionally substituted $C_{5-10}$ heterocycle. In a sub-embodiment of this invention $R^1$ is optionally substituted $C_{5-10}$ heterocycle selected from the group consisting of optionally substituted pyrazolyl, pyridyl, imidazolyl, imidazopyridinyl, thiazolyl, isoxazolyl, triazolyl, oxazolyl, pyrimidinyl, pyrrolopyridinyl, imidazothiazolyl, and pyrazoloquinolinyl. A subembodiment of this invention is realized when $R^1$ is optionally substituted pyrazolyl. Another subembodiment is realized when $R^1$ is optionally substituted pyridyl. Still another subembodiment of this invention is realized when $R^1$ is optionally substituted imidazolyl. Another subembodiment is realized when $R^1$ is optionally substituted imidazopyridinyl. Still another subembodiment of this invention is realized when $R^1$ is optionally substituted pyrimidinyl.

Still in another embodiment of this invention $R^a$ represents —CN, —$C_{1-4}$haloalkyl, —OC$_{1-4}$haloalkyl, SCF$_3$, —$C_{1-6}$alkyl, —$(CHR)_nC_{6-10}$ aryl, —$(CHR)_nC_{5-10}$ heterocycle, —$C_{3-10}$ cycloalkyl, —O$(CH_2)_nC_{6-10}$ aryl, —O—$C_{5-10}$ heterocycle, —O—, —$(CH_2)_n$halo, —OR, —NRR, —C(O)NRR, or —COR, said aryl and heterocycle optionally substituted with 1 to 3 groups of $R^b$. A subembodiment of this invention is realized when $R^a$ represents —CN, —CF$_3$, —OCF$_3$, SCF$_3$, —$C_{1-6}$alkyl, —$(CH_2)_n$halo, NRR, —C(O)NRR, pyrazolyl, furanyl, phenyl, pyridyl, tetrazolyl, oxazolyl, thiazolyl, pyrrolyl, triazolyl, imidazolyl, oxadiazolyl, thiadiazolyl, or O$(CH_2)_n$phenyl, said pyrazolyl, furanyl, phenyl, pyridyl, tetrazolyl, oxazolyl, thiazolyl, pyrrolyl, triazolyl, imidazolyl, oxadiazolyl, thiadiazolyl, and O$(CH_2)_n$ phenyl optionally substituted with 1 to 3 groups of $R^b$.

Yet another embodiment of this invention is realized when $R^b$ represents, —$C_{1-6}$alkyl, —$(CH_2)_nC_{1-4}$haloalkyl, OR, CN, halo, or —$C_{3-10}$ cycloalkyl.

In still another embodiment of this invention $R^1$ is optionally substituted $C_{5-10}$ heterocycle selected from the group consisting of pyrazolyl, pyridyl, imidazolyl, imidazopyridinyl, thiazolyl, isoxazolyl, triazolyl, oxazolyl, pyrimidinyl, pyrrolopyridinyl, imidazothiazolyl, and pyrazoloquinolinyl, said groups optionally substituted with 1 to 3 groups of $R^a$ selected from the group consisting of —CN, —CF$_3$, —OCF$_3$, SCF$_3$, —$C_{1-6}$alkyl, —$(CH_2)_n$halo, NRR, —C(O)NRR, pyrazolyl, furanyl, phenyl, pyridyl, tetrazolyl, oxazolyl, thiazolyl, pyrrolyl, triazolyl, imidazolyl, oxadiazolyl, thiadiazolyl, and O$(CH_2)_n$phenyl, said pyrazolyl, furanyl, phenyl, pyridyl, tetrazolyl, oxazolyl, thiazolyl, pyrrolyl, triazolyl, imidazolyl, oxadiazolyl, thiadiazolyl, and O$(CH_2)_n$ phenyl optionally substituted with 1 to 3 groups of $R^b$.

Another embodiment of the invention is realized when the compounds are represented by formula I:

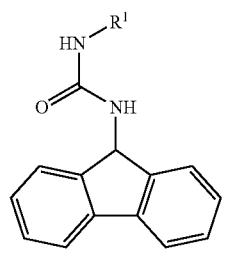

or pharmaceutically acceptable salts thereof, wherein all variables are as described herein.

In another embodiment of the invention the compounds of formula I is represented by structural formula II:

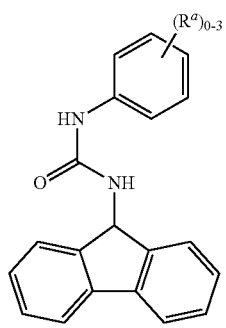

II or pharmaceutically acceptable salts there of wherein $R^a$ is as previously described. A subembodiment of the invention of structural formula II is realized when $R^a$ is selected from the group consisting of —CN, —CF$_3$, —OCF$_3$, SCF$_3$, —C$_{1-6}$alkyl, —(CH$_2$)$_n$halo, NRR, —C(O)NRR, pyrazolyl, furanyl, phenyl, pyridyl, tetrazolyl, oxazolyl, thiazolyl, pyrrolyl, triazolyl, imidazolyl, oxadiazolyl, thiadiazolyl, and O(CH$_2$)$_n$phenyl, said pyrazolyl, furanyl, phenyl, pyridyl, tetrazolyl, oxazolyl, thiazolyl, pyrrolyl, triazolyl, imidazolyl, oxadiazolyl, thiadiazolyl, and O(CH$_2$)$_n$phenyl optionally substituted with 1 to 3 groups of $R^b$.

In another embodiment of the invention the compounds of formula I is represented by structural formula III:

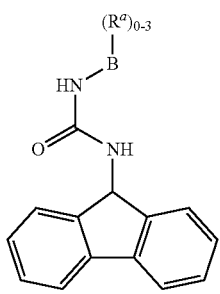

III or pharmaceutically acceptable salts there of wherein B is pyrazolyl or imidazolyl and $R^a$ is as previously described. A subembodiment of the invention of formula III is realized when B is pyrazolyl and $R^a$ is selected from the group consisting of —CN, —CF$_3$, —OCF$_3$, SCF$_3$, —C$_{1-6}$alkyl, —(CH$_2$)$_n$halo, NRR, —C(O)NRR, pyrazolyl, furanyl, phenyl, pyridyl, tetrazolyl, oxazolyl, thiazolyl, pyrrolyl, triazolyl, imidazolyl, oxadiazolyl, thiadiazolyl, and O(CH$_2$)$_n$phenyl, said pyrazolyl, furanyl, phenyl, pyridyl, tetrazolyl, oxazolyl, thiazolyl, pyrrolyl, triazolyl, imidazolyl, oxadiazolyl, thiadiazolyl, and O(CH$_2$)$_n$phenyl optionally substituted with 1 to 3 groups of $R^b$. Still another subembodiment of the invention of formula III is realized when B is imidazolyl and $R^a$ is selected from the group consisting of —CN, —CF$_3$, —OCF$_3$, SCF$_3$, —C$_{1-6}$alkyl, —(CH$_2$)$_n$halo, NRR, —C(O)NRR, pyrazolyl, furanyl, phenyl, pyridyl, tetrazolyl, oxazolyl, thiazolyl, pyrrolyl, triazolyl, imidazolyl, oxadiazolyl, thiadiazolyl, and O(CH$_2$)$_n$phenyl, said pyrazolyl, furanyl, phenyl, pyridyl, tetrazolyl, oxazolyl, thiazolyl, pyrrolyl, triazolyl, imidazolyl, oxadiazolyl, thiadiazolyl, and O(CH$_2$)$_n$phenyl optionally substituted with 1 to 3 groups of $R^b$.

Still in another embodiment the compounds of formula I are represented by structural formula IV:

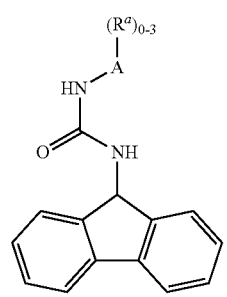

IV or pharmaceutically acceptable salts there of wherein A is pyridyl or pyrimidinyl and $R^a$ is as previously described. A subembodiment of the invention of formula IV is realized when A is pyridyl and $R^a$ is selected from the group consisting of —CN, —CF$_3$, —OCF$_3$, SCF$_3$, —C$_{1-6}$alkyl, —(CH$_2$)$_n$halo, NRR, —C(O)NRR, pyrazolyl, furanyl, phenyl, pyridyl, tetrazolyl, oxazolyl, thiazolyl, pyrrolyl, triazolyl, imidazolyl, oxadiazolyl, thiadiazolyl, and O(CH$_2$)$_n$phenyl, said pyrazolyl, furanyl, phenyl, pyridyl, tetrazolyl, oxazolyl, thiazolyl, pyrrolyl, triazolyl, imidazolyl, oxadiazolyl, thiadiazolyl, and O(CH$_2$)$_n$phenyl, optionally substituted with 1 to 3 groups of $R^b$. Another subembodiment of the invention of formula IV is realized when A is pyrimidinyl and $R^a$ is selected from the group consisting of —CN, —CF$_3$, —OCF$_3$, SCF$_3$, —C$_{1-6}$alkyl, —(CH$_2$)$_n$halo, NRR, —C(O)NRR, pyrazolyl, furanyl, phenyl, pyridyl, tetrazolyl, oxazolyl, thiazolyl, pyrrolyl, triazolyl, imidazolyl, oxadiazolyl, thiadiazolyl, and O(CH$_2$)$_n$phenyl, said pyrazolyl, furanyl, phenyl, pyridyl, tetrazolyl, oxazolyl, thiazolyl, pyrrolyl, triazolyl, imidazolyl, oxadiazolyl, thiadiazolyl, and O(CH$_2$)$_n$phenyl, optionally substituted with 1 to 3 groups of $R^b$.

Still in another embodiment the compounds of formula I are represented by structural formula Ia:

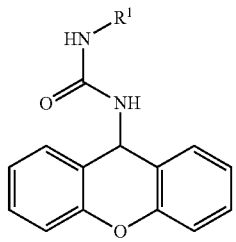

V wherein $R^1$ is as previously described or pharmaceutically acceptable salts thereof. A subembodiment of the invention of formula V wherein $R^a$ is selected from the group consisting of —CN, —CF$_3$, —OCF$_3$, SCF$_3$, —C$_{1-6}$alkyl, —(CH$_2$)$_n$halo, NRR, —C(O)NRR, pyrazolyl, furanyl, phenyl, pyridyl, tetrazolyl, oxazolyl, thiazolyl, pyrrolyl, triazolyl, imidazolyl, oxadiazolyl, thiadiazolyl, and O(CH$_2$)$_n$phenyl, said pyrazolyl, furanyl, phenyl, pyridyl, tetrazolyl, oxazolyl, thiazolyl, pyrrolyl, triazolyl, imidazolyl, oxadiazolyl, thiadiazolyl, and O(CH$_2$)$_n$phenyl, optionally substituted with 1 to 3 groups of $R^b$.

Examples of compounds of this invention include those in Table 1:

TABLE 1

| Compound | Structure | IUPAC Name | Exact Mass [M + H]+ |
|---|---|---|---|
| 1 | 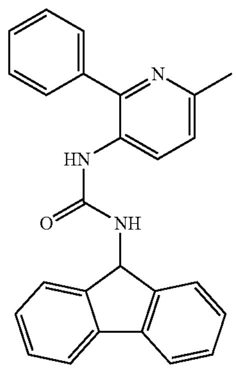 [SMILES: Cc1ccc(NC(=O)NC2c3ccccc3-c3ccccc32)c(-c2ccccc2)n1] | 1-(9H-fluoren-9-yl)-3-(6-methyl-2-phenylpyridin-3-yl)urea | 392.1748 |
| 2 | 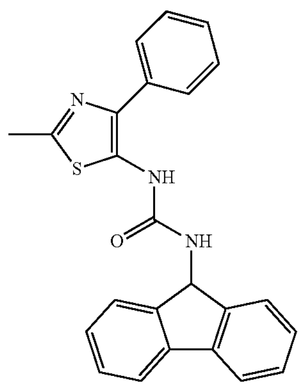 [SMILES: Cc1nc(-c2ccccc2)c(NC(=O)NC2c3ccccc3-c3ccccc32)s1] | 1-(9H-fluoren-9-yl)-3-(2-methyl-4-phenyl-1,3-thiazol-5-yl)urea | 398.0 |
| 3 | 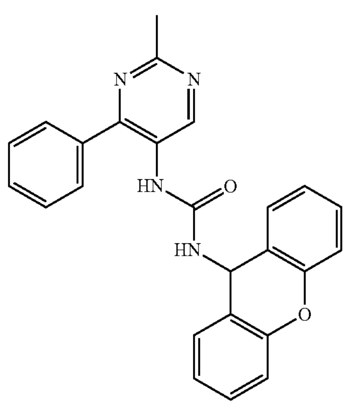 [SMILES: Cc1ncc(NC(=O)NC2c3ccccc3Oc3ccccc32)c(-c2ccccc2)n1] | 1-(2-methyl-4-phenylpyrimidin-5-yl)-3-(9H-xanthen-9-yl)urea | 409.1 |
| 4 | 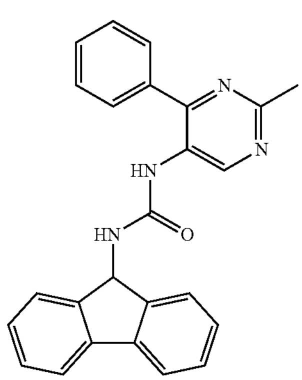 [SMILES: Cc1ncc(NC(=O)NC2c3ccccc3-c3ccccc32)c(-c2ccccc2)n1] | 1-(9H-fluoren-9-yl)-3-(2-methyl-4-phenylpyrimidin-5-yl)urea | 393.1702 |

TABLE 1-continued

| Compound | Structure | IUPAC Name | Exact Mass [M + H]+ |
|---|---|---|---|
| 5 | 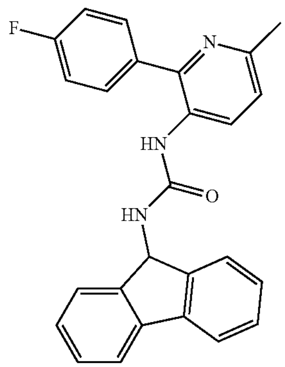 [SMILES: Cc1ccc(NC(=O)NC2c3ccccc3-c3ccccc32)c(-c2ccc(F)cc2)n1] | 1-(9H-fluoren-9-yl)-3-[2-(4-fluorophenyl)-6-methylpyridin-3-yl]urea | 410.1652 |
| 6 | 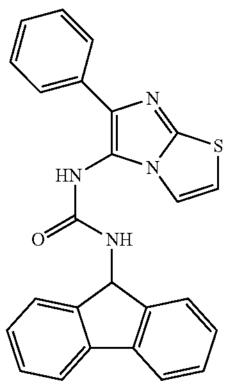 [SMILES: O=C(Nc1c(-c2ccccc2)nc2sccn12)NC1c2ccccc2-c2ccccc21] | 1-(9H-fluoren-9-yl)-3-(6-phenylimidazo[2,1-b][1,3]thiazol-5-yl)urea | 423.1267 |
| 7 | 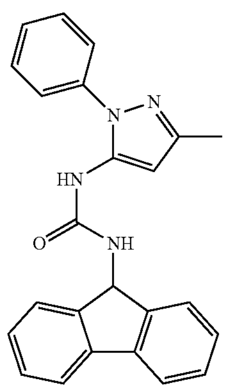 [SMILES: Cc1cc(NC(=O)NC2c3ccccc3-c3ccccc32)n(-c2ccccc2)n1] | 1-(9H-fluoren-9-yl)-3-(3-methyl-1-phenyl-1H-pyrazol-5-yl)urea | 381.1701 |
| 8 | 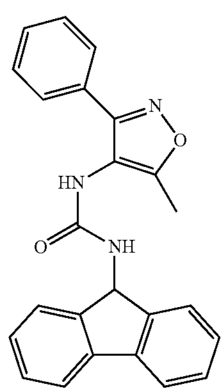 [SMILES: Cc1onc(-c2ccccc2)c1NC(=O)NC1c2ccccc2-c2ccccc21] | 1-(9H-fluoren-9-yl)-3-(5-methyl-3-phenylisoxazol-4-yl)urea | 382.1542 |

TABLE 1-continued

| Compound | Structure | IUPAC Name | Exact Mass [M + H]+ |
|---|---|---|---|
| 9 | 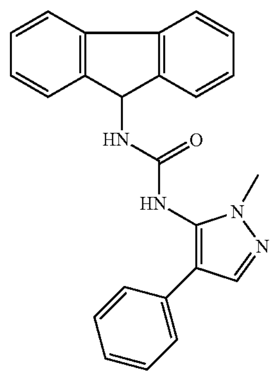 [SMILES: Cn1ncc(-c2ccccc2)c1NC(=O)NC1c2ccccc2-c2ccccc21] | 1-(9H-fluoren-9-yl)-3-(1-methyl-4-phenyl-1H-pyrazol-5-yl)urea | 381.1701 |
| 10 | 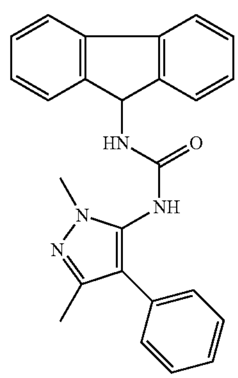 [SMILES: Cc1nn(C)c(NC(=O)NC2c3ccccc3-c3ccccc32)c1-c1ccccc1] | 1-(1,3-dimethyl-4-phenyl-1H-pyrazol-5-yl)-3-(9H-fluoren-9-yl)urea | 395.1858 |
| 11 | 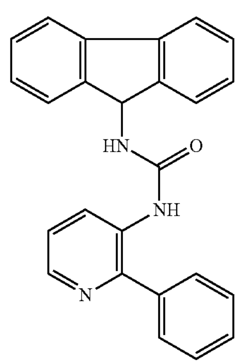 [SMILES: O=C(Nc1cccnc1-c1ccccc1)NC1c2ccccc2-c2ccccc21] | 1-(9H-fluoren-9-yl)-3-(2-phenylpyridin-3-yl)urea | 378.1 |
| 12 | 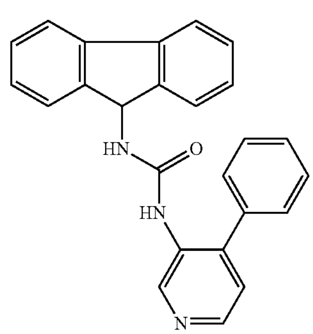 [SMILES: O=C(Nc1cnccc1-c1ccccc1)NC1c2ccccc2-c2ccccc21] | 1-(9H-fluoren-9-yl)-3-(4-phenylpyridin-3-yl)urea | 378.1594 |

TABLE 1-continued

| Compound | Structure | IUPAC Name | Exact Mass [M + H]+ |
|---|---|---|---|
| 13 | 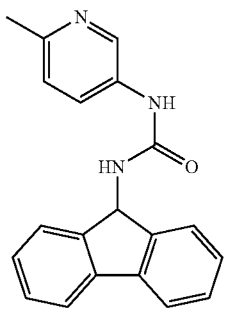 [SMILES: Cc1ccc(NC(=O)NC2c3ccccc3-c3ccccc32)cn1] | 1-(9H-fluoren-9-yl)-3-(6-methylpyridin-3-yl)urea | 316.1 |
| 14 | 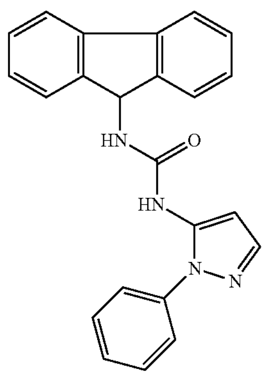 [SMILES: O=C(Nc1ccnn1-c1ccccc1)NC1c2ccccc2-c2ccccc21] | 1-(9H-fluoren-9-yl)-3-(1-phenyl-1H-pyrazol-5-yl)urea | 367.85 |
| 15 | 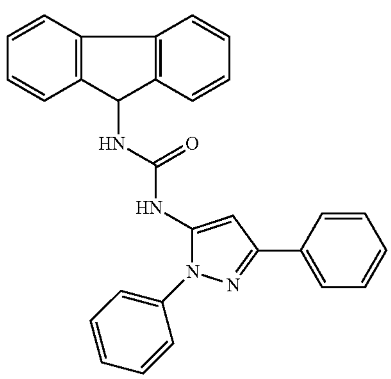 [SMILES: O=C(Nc1cc(-c2ccccc2)nn1-c1ccccc1)NC1c2ccccc2-c2ccccc21] | 1-(1,3-diphenyl-1H-pyrazol-5-yl)-3-(9H-fluoren-9-yl)urea | 443.18 |
| 16 | 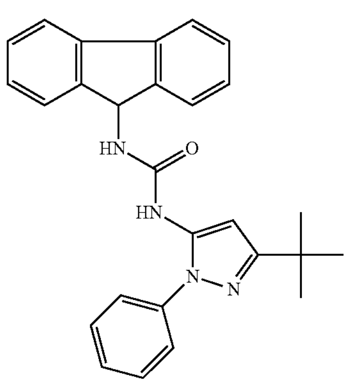 [SMILES: CC(C)(C)c1cc(NC(=O)NC2c3ccccc3-c3ccccc32)n(-c2ccccc2)n1] | 1-(3-tert-butyl-1-phenyl-1H-pyrazol-5-yl)-3-(9H-fluoren-9-yl)urea | 423.92 |

TABLE 1-continued

| Compound | Structure | IUPAC Name | Exact Mass [M + H]+ |
|---|---|---|---|
| 17 | 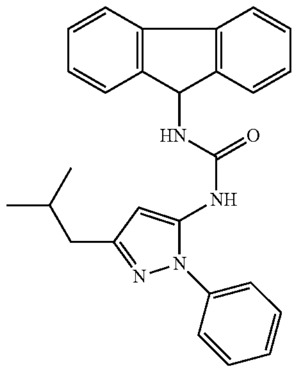 [SMILES: CC(C)Cc1cc(NC(=O)NC2c3ccccc3-c3ccccc32)n(-c2ccccc2)n1] | 1-(9H-fluoren-9-yl)-3-[3-(2-methylpropyl)-1-phenyl-1H-pyrazol-5-yl]urea | 423.21 |
| 18 | 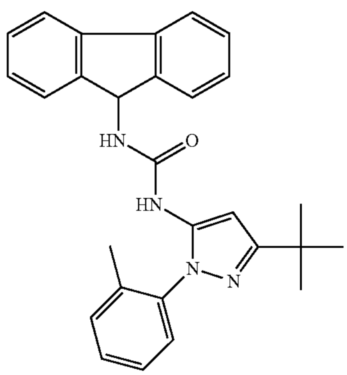 [SMILES: Cc1ccccc1-n1nc(C(C)(C)C)cc1NC(=O)NC1c2ccccc2-c2ccccc21] | 1-[3-tert-butyl-1-(2-methylphenyl)-1H-pyrazol-5-yl]-3-(9H-fluoren-9-yl)urea | 437.23 |
| 19 | 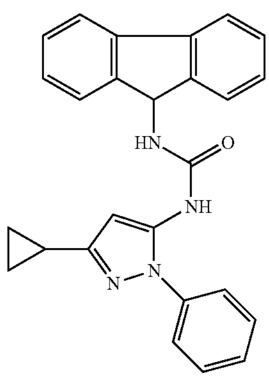 [SMILES: O=C(Nc1cc(C2CC2)nn1-c1ccccc1)NC1c2ccccc2-c2ccccc21] | 1-(3-cyclopropyl-1-phenyl-1H-pyrazol-5-yl)-3-(9H-fluoren-9-yl)urea | 407.88 |
| 20 | 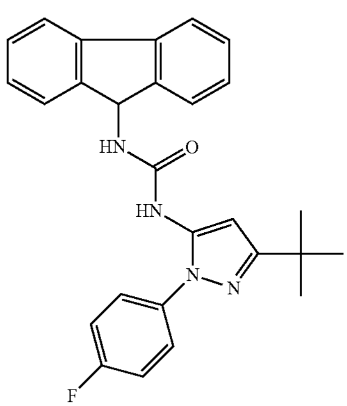 [SMILES: CC(C)(C)c1cc(NC(=O)NC2c3ccccc3-c3ccccc32)n(-c2ccc(F)cc2)n1] | 1-[3-tert-butyl-1-(4-fluorophenyl)-1H-pyrazol-5-yl]-3-(9H-fluoren-9-yl)urea | 441.2 |

TABLE 1-continued

| Compound | Structure | IUPAC Name | Exact Mass [M + H]+ |
|---|---|---|---|
| 21 | 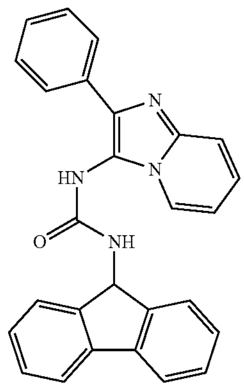 [SMILES: O=C(Nc1c(-c2ccccc2)nc2ccccn12)NC1c2ccccc2-c2ccccc21] | 1-(9H-fluoren-9-yl)-3-(2-phenylimidazo[1,2-a]pyridin-3-yl)urea | 417.0 |
| 22 | 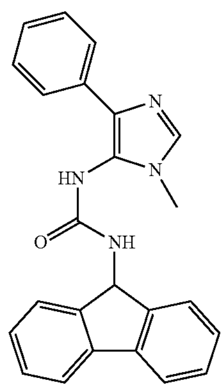 [SMILES: Cn1cnc(-c2ccccc2)c1NC(=O)NC1c2ccccc2-c2ccccc21] | 1-(9H-fluoren-9-yl)-3-(1-methyl-4-phenyl-1H-imidazol-5-yl)urea | 381.1 |
| 23 | 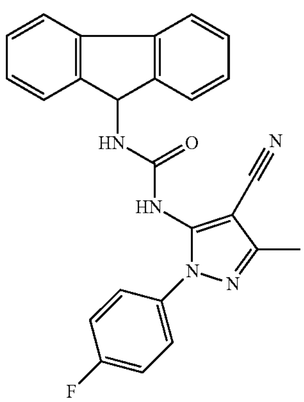 [SMILES: Cc1nn(-c2ccc(F)cc2)c(NC(=O)NC2c3ccccc3-c3ccccc32)c1C#N] | 1-[4-cyano-1-(4-fluorophenyl)-3-methyl-1H-pyrazol-5-yl]-3-(9H-fluoren-9-yl)urea | 424.15 |
| 24 | 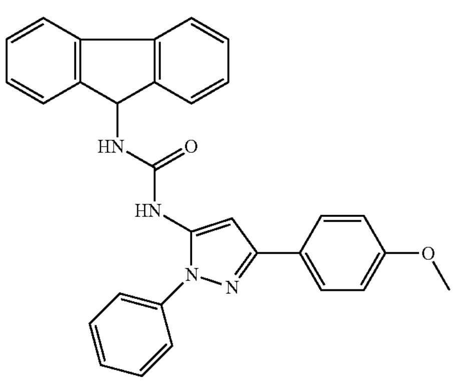 [SMILES: COc1ccc(-c2cc(NC(=O)NC3c4ccccc4-c4ccccc43)n(-c3ccccc3)n2)cc1] | 1-(9H-fluoren-9-yl)-3-[3-(4-methoxyphenyl)-1-phenyl-1H-pyrazol-5-yl]urea | 473.19 |

TABLE 1-continued

| Compound | Structure | IUPAC Name | Exact Mass [M + H]+ |
|---|---|---|---|
| 25 | 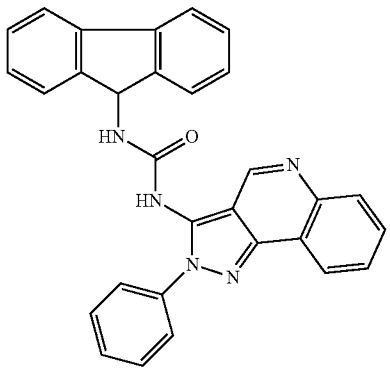 [SMILES: O=C(Nc1c2cnc3ccccc3c2nn1-c1ccccc1)NC1c2ccccc2-c2ccccc21] | 1-(9H-fluoren-9-yl)-3-(2-phenyl-2H-pyrazolo[4,3-c]quinolin-3-yl)urea | 468.17 |
| 26 | 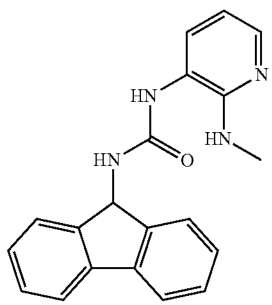 [SMILES: CNc1ncccc1NC(=O)NC1c2ccccc2-c2ccccc21] | 1-(9H-fluoren-9-yl)-3-[2-(methylamino)pyridin-3-yl]urea | 331.1 |
| 27 | 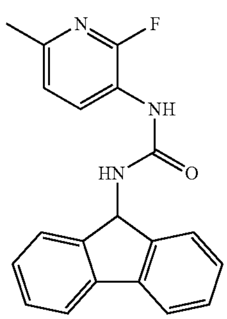 [SMILES: Cc1ccc(NC(=O)NC2c3ccccc3-c3ccccc32)c(F)n1] | 1-(9H-fluoren-9-yl)-3-(2-fluoro-6-methylpyridin-3-yl)urea | 334.1 |
| 28 | 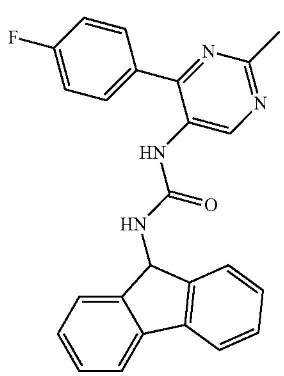 [SMILES: Cc1ncc(NC(=O)NC2c3ccccc3-c3ccccc32)c(-c2ccc(F)cc2)n1] | 1-(9H-fluoren-9-yl)-3-[4-(4-fluorophenyl)-2-methylpyrimidin-5-yl]urea | 411.0 |

TABLE 1-continued

| Compound | Structure | IUPAC Name | Exact Mass [M + H]+ |
|---|---|---|---|
| 29 | 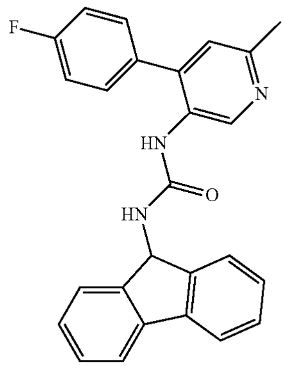 [SMILES: Cc1cc(-c2ccc(F)cc2)c(NC(=O)NC2c3ccccc3-c3ccccc32)cn1] | 1-(9H-fluoren-9-yl)-3-[4-(4-fluorophenyl)-6-methylpyridin-3-yl]urea | 410.455 |
| 30 | 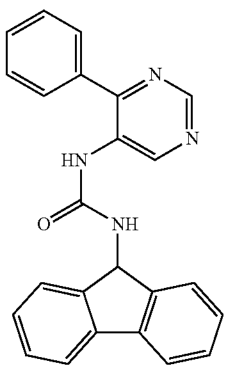 [SMILES: O=C(Nc1cncnc1-c1ccccc1)NC1c2ccccc2-c2ccccc21] | 1-(9H-fluoren-9-yl)-3-(4-phenylpyrimidin-5-yl)urea | 379.0 |
| 31 | 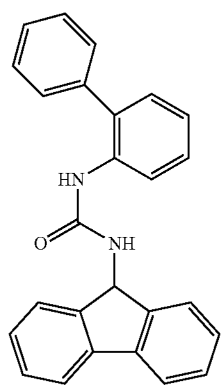 [SMILES: O=C(Nc1ccccc1-c1ccccc1)NC1c2ccccc2-c2ccccc21] | 1-biphenyl-2-yl-3-(9H-fluoren-9-yl)urea | 377.1 |
| 32 | 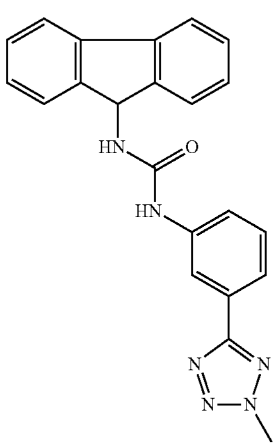 [SMILES: Cn1nnc(-c2cccc(NC(=O)NC3c4ccccc4-c4ccccc43)c2)n1] | 1-(9H-fluoren-9-yl)-3-[3-(2-methyl-2H-tetrazol-5-yl)phenyl]urea | 383.1 |

TABLE 1-continued

| Compound | Structure | IUPAC Name | Exact Mass [M + H]+ |
|---|---|---|---|
| 33 | 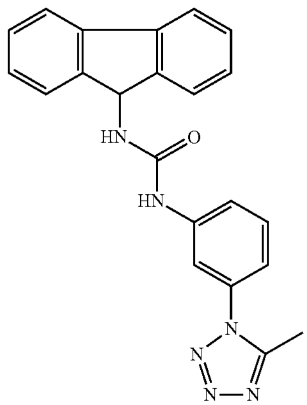 [SMILES: Cc1nnnn1-c1cccc(NC(=O)NC2c3ccccc3-c3ccccc32)c1] | 1-(9H-fluoren-9-yl)-3-[3-(5-methyl-1H-tetrazol-1-yl)phenyl]urea | 383.1 |
| 34 | 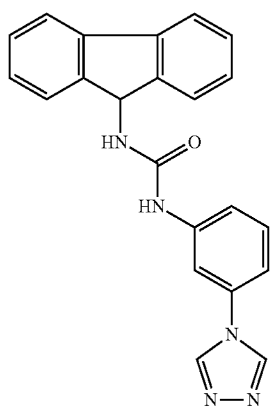 [SMILES: O=C(Nc1cccc(-n2cnnc2)c1)NC1c2ccccc2-c2ccccc21] | 1-(9H-fluoren-9-yl)-3-[3-(4H-1,2,4-triazol-4-yl)phenyl]urea | 368.1 |
| 35 | 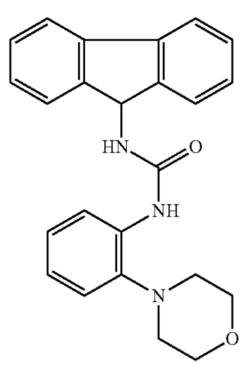 [SMILES: O=C(Nc1ccccc1N1CCOCC1)NC1c2ccccc2-c2ccccc21] | 1-(9H-fluoren-9-yl)-3-(2-morpholin-4-ylphenyl)urea | 386.1 |
| 36 | 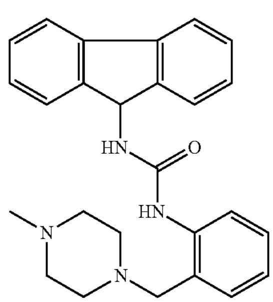 [SMILES: CN1CCN(Cc2ccccc2NC(=O)NC2c3ccccc3-c3ccccc32)CC1] | 1-(9H-fluoren-9-yl)-3-{2-[(4-methylpiperazin-1-yl)methyl]phenyl}urea | 413.1 |

TABLE 1-continued

| Compound | Structure | IUPAC Name | Exact Mass [M + H]+ |
|---|---|---|---|
| 37 | 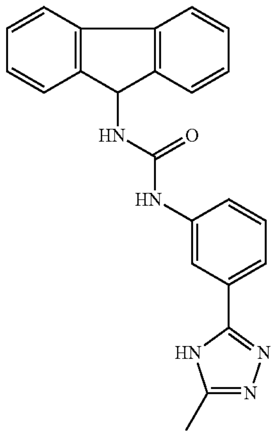 [SMILES: Cc1nnc(-c2cccc(NC(=O)NC3c4ccccc4-c4ccccc43)c2)[nH]1] | 1-(9H-fluoren-9-yl)-3-[3-(5-methyl-4H-1,2,4-triazol-3-yl)phenyl]urea | 382.1 |
| 38 | 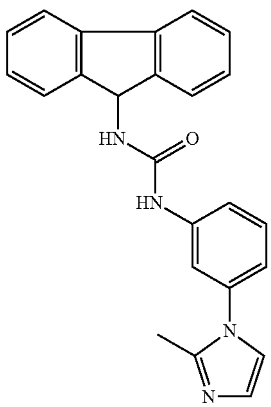 [SMILES: Cc1nccn1-c1cccc(NC(=O)NC2c3ccccc3-c3ccccc32)c1] | 1-(9H-fluoren-9-yl)-3-[3-(2-methyl-1H-imidazol-1-yl)phenyl]urea | 381.1 |
| 39 | 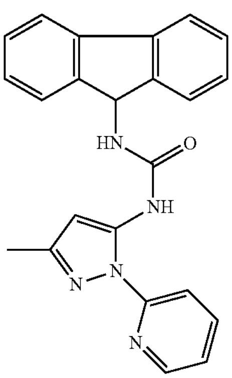 [SMILES: Cc1cc(NC(=O)NC2c3ccccc3-c3ccccc32)n(-c2ccccn2)n1] | 1-(9H-fluoren-9-yl)-3-(3-methyl-1-pyridin-2-yl-1H-pyrazol-5-yl)urea | 382.1 |
| 40 | 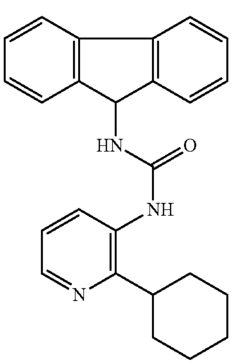 [SMILES: O=C(Nc1cccnc1C1CCCCC1)NC1c2ccccc2-c2ccccc21] | 1-(2-cyclohexylpyridin-3-yl)-3-(9H-fluoren-9-yl)urea | 384.1 |

TABLE 1-continued

| Compound | Structure | IUPAC Name | Exact Mass [M + H]+ |
|---|---|---|---|
| 41 | 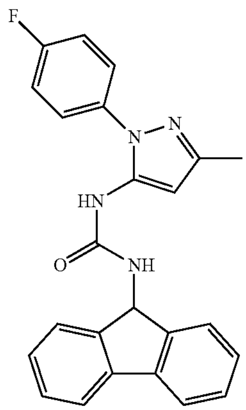 [SMILES: Cc1cc(NC(=O)NC2c3ccccc3-c3ccccc32)n(-c2ccc(F)cc2)n1] | 1-(9H-fluoren-9-yl)-3-[1-(4-fluorophenyl)-3-methyl-1H-pyrazol-5-yl]urea | 399.1 |
| 42 | 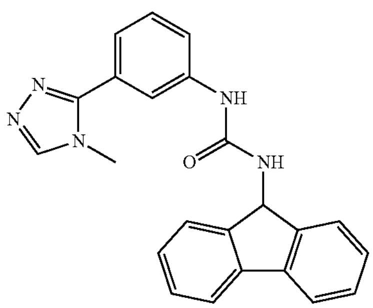 [SMILES: Cn1cnnc1-c1cccc(NC(=O)NC2c3ccccc3-c3ccccc32)c1] | 1-(9H-fluoren-9-yl)-3-[3-(4-methyl-4H-1,2,4-triazol-3-yl)phenyl]urea | 382.1 |
| 43 | 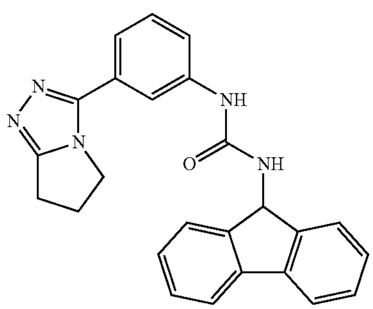 [SMILES: O=C(Nc1cccc(-c2nnc3n2CCC3)c1)NC1c2ccccc2-c2ccccc21] | 1-[3-(6,7-dihydro-5H-pyrrolo[2,1-c][1,2,4]triazol-3-yl)phenyl]-3-(9H-fluoren-9-yl)urea | 408.467 |
| 44 | 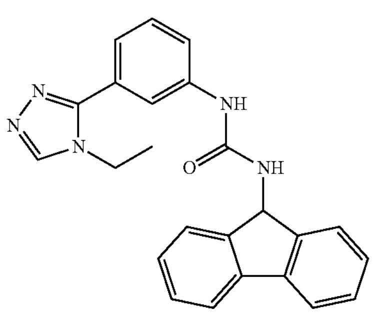 [SMILES: CCn1cnnc1-c1cccc(NC(=O)NC2c3ccccc3-c3ccccc32)c1] | 1-[3-(4-ethyl-4H-1,2,4-triazol-3-yl)phenyl]-3-(9H-fluoren-9-yl)urea | 396.456 |

TABLE 1-continued

| Compound | Structure | IUPAC Name | Exact Mass [M + H]+ |
|---|---|---|---|
| 45 | 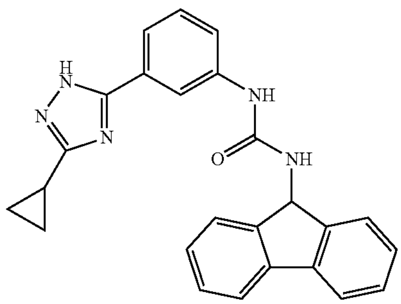 [SMILES: O=C(Nc1cccc(-c2nc(C3CC3)n[nH]2)c1)NC1c2ccccc2-c2ccccc21] | 1-[3-(3-cyclopropyl-1H-1,2,4-triazol-5-yl)phenyl]-3-(9H-fluoren-9-yl)urea | 408.467 |
| 46 | 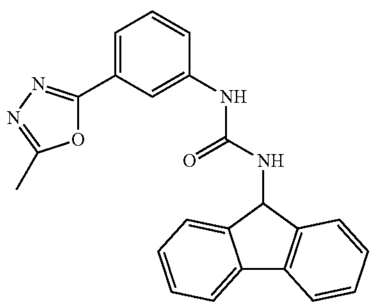 [SMILES: Cc1nnc(-c2cccc(NC(=O)NC3c4ccccc4-c4ccccc43)c2)o1] | 1-(9H-fluoren-9-yl)-3-[3-(5-methyl-1,3,4-oxadiazol-2-yl)phenyl]urea | 383.3 |
| 47 | 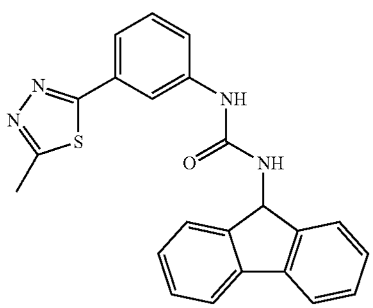 [SMILES: Cc1nnc(-c2cccc(NC(=O)NC3c4ccccc4-c4ccccc43)c2)s1] | 1-(9H-fluoren-9-yl)-3-[3-(5-methyl-1,3,4-thiadiazol-2-yl)phenyl]urea | 399.48 |
| 48 | 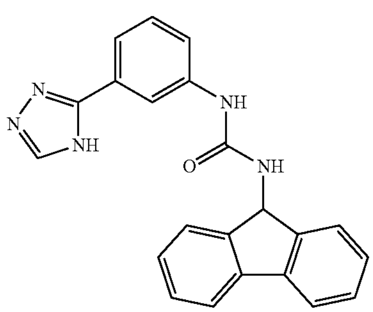 [SMILES: O=C(Nc1cccc(-c2nnc[nH]2)c1)NC1c2ccccc2-c2ccccc21] | 1-(9H-fluoren-9-yl)-3-[3-(4H-1,2,4-triazol-3-yl)phenyl]urea | 368.1 |
| 49 | 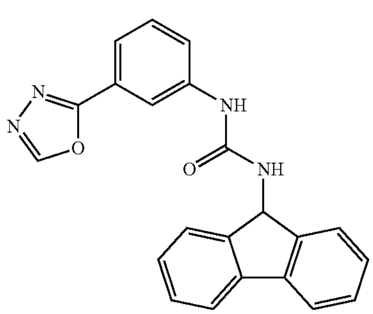 [SMILES: O=C(Nc1cccc(-c2nnco2)c1)NC1c2ccccc2-c2ccccc21] | 1-(9H-fluoren-9-yl)-3-[3-(1,3,4-oxadiazol-2-yl)phenyl]urea | 369.38 |

TABLE 1-continued

| Compound | Structure | IUPAC Name | Exact Mass [M + H]+ |
|---|---|---|---|
| 50 | 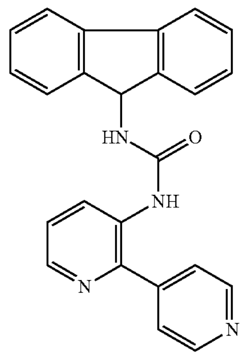 [SMILES: O=C(Nc1cccnc1-c1ccncc1)NC1c2ccccc2-c2ccccc21] | 1-(2,4'-bipyridin-3-yl)-3-(9H-fluoren-9-yl)urea | 379.1 |
| 51 | 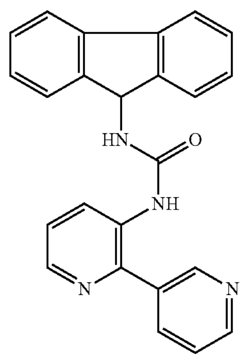 [SMILES: O=C(Nc1cccnc1-c1cccnc1)NC1c2ccccc2-c2ccccc21] | 1-(2,3'-bipyridin-3-yl)-3-(9H-fluoren-9-yl)urea | 379.1 |
| 52 | 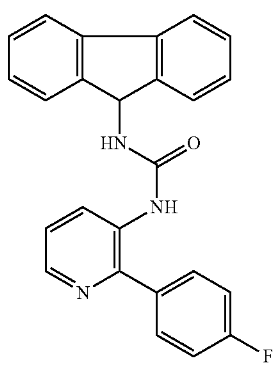 [SMILES: O=C(Nc1cccnc1-c1ccc(F)cc1)NC1c2ccccc2-c2ccccc21] | 1-(9H-fluoren-9-yl)-3-[2-(4-fluorophenyl)pyridin-3-yl]urea | 396.1 |
| 53 | 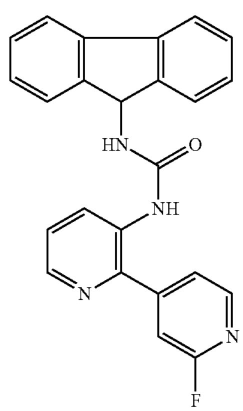 [SMILES: O=C(Nc1cccnc1-c1ccnc(F)c1)NC1c2ccccc2-c2ccccc21] | 1-(9H-fluoren-9-yl)-3-(2'-fluoro-2,4'-bipyridin-3-yl)urea | 397.1 |

TABLE 1-continued

| Compound | Structure | IUPAC Name | Exact Mass [M + H]+ |
|---|---|---|---|
| 54 | 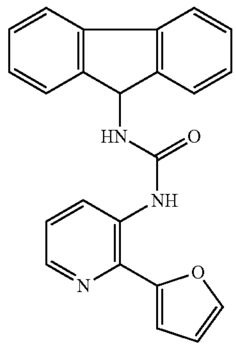 [SMILES: O=C(Nc1cccnc1-c1ccco1)NC1c2ccccc2-c2ccccc21] | 1-(9H-fluoren-9-yl)-3-(2-furan-2-ylpyridin-3-yl)urea | 368.1 |
| 55 | 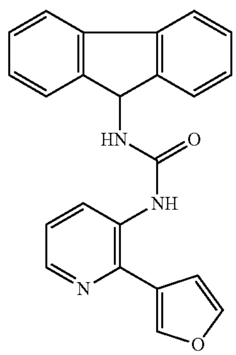 [SMILES: O=C(Nc1cccnc1-c1ccoc1)NC1c2ccccc2-c2ccccc21] | 1-(9H-fluoren-9-yl)-3-(2-furan-3-ylpyridin-3-yl)urea | 368.1 |
| 56 | 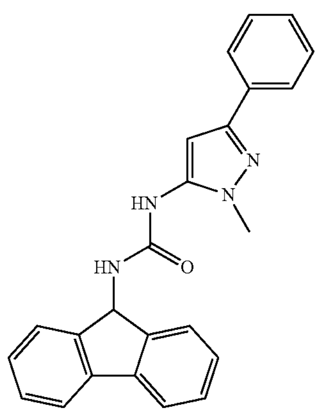 [SMILES: Cn1nc(-c2ccccc2)cc1NC(=O)NC1c2ccccc2-c2ccccc21] | 1-(9H-fluoren-9-yl)-3-(1-methyl-3-phenyl-1H-pyrazol-5-yl)urea | 381.442 |
| 57 | 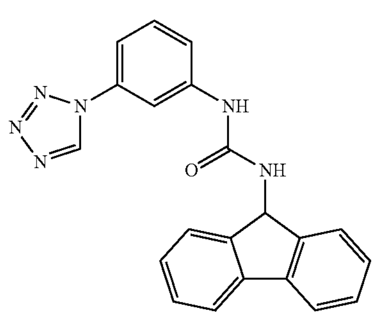 [SMILES: O=C(Nc1cccc(-n2cnnn2)c1)NC1c2ccccc2-c2ccccc21] | 1-(9H-fluoren-9-yl)-3-[3-(1H-tetrazol-1-yl)phenyl]urea | 369.39 |

TABLE 1-continued

| Compound | Structure | IUPAC Name | Exact Mass [M + H]+ |
|---|---|---|---|
| 58 | 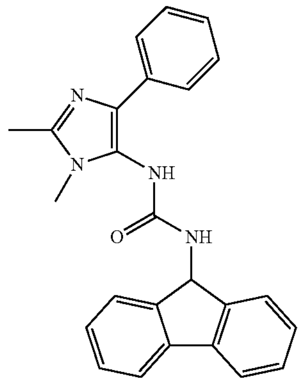 [SMILES: Cc1nc(-c2ccccc2)c(NC(=O)NC2c3ccccc3-c3ccccc32)n1C] | 1-(1,2-dimethyl-4-phenyl-1H-imidazol-5-yl)-3-(9H-fluoren-9-yl)urea | 395.17 |
| 59 | 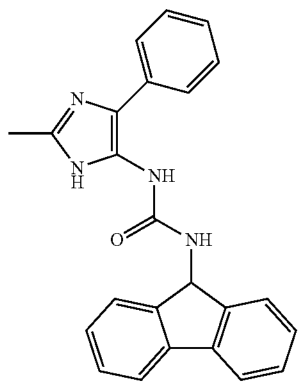 [SMILES: Cc1nc(-c2ccccc2)c(NC(=O)NC2c3ccccc3-c3ccccc32)[nH]1] | 1-(9H-fluoren-9-yl)-3-(2-methyl-4-phenyl-1H-imidazol-5-yl)urea | 381.14 |
| 60 | 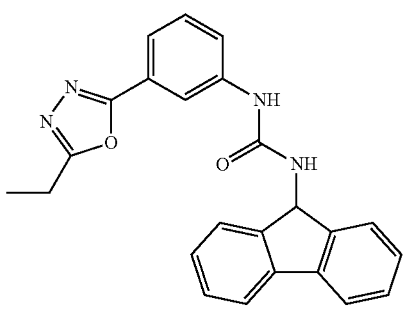 [SMILES: CCc1nnc(-c2cccc(NC(=O)NC3c4ccccc4-c4ccccc43)c2)o1] | 1-[3-(5-ethyl-1,3,4-oxadiazol-2-yl)phenyl]-3-(9H-fluoren-9-yl)urea | 397.441 |
| 61 | 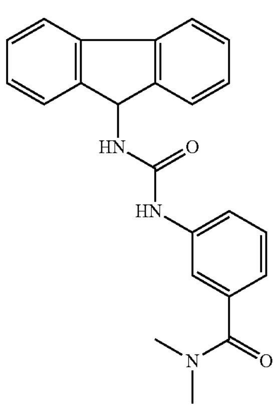 [SMILES: CN(C)C(=O)c1cccc(NC(=O)NC2c3ccccc3-c3ccccc32)c1] | 3-[(9H-fluoren-9-ylcarbamoyl)amino]-N,N-dimethylbenzamide | 372.1 |

TABLE 1-continued

| Compound | Structure | IUPAC Name | Exact Mass [M + H]+ |
|---|---|---|---|
| 62 | 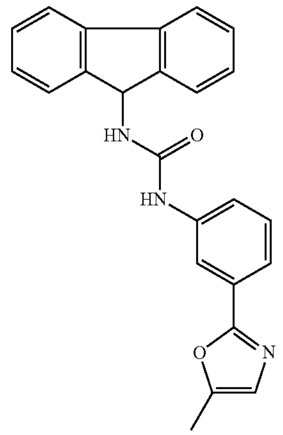 [SMILES: Cc1cnc(-c2cccc(NC(=O)NC3c4ccccc4-c4ccccc43)c2)o1] | 1-(9H-fluoren-9-yl)-3-[3-(5-methyl-1,3-oxazol-2-yl)phenyl]urea | 382.1 |
| 63 | 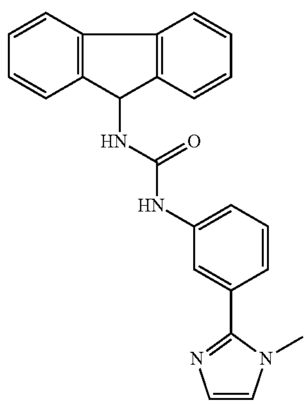 [SMILES: Cn1ccnc1-c1cccc(NC(=O)NC2c3ccccc3-c3ccccc32)c1] | 1-(9H-fluoren-9-yl)-3-[3-(1-methyl-1H-imidazol-2-yl)phenyl]urea | 381.1 |
| 64 | 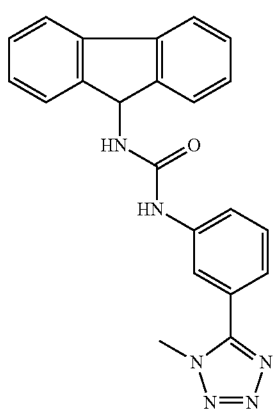 [SMILES: Cn1nnnc1-c1cccc(NC(=O)NC2c3ccccc3-c3ccccc32)c1] | 1-(9H-fluoren-9-yl)-3-[3-(1-methyl-1H-tetrazol-5-yl)phenyl]urea | 383.1 |

TABLE 1-continued

| Compound | Structure | IUPAC Name | Exact Mass [M + H]+ |
|---|---|---|---|
| 65 | 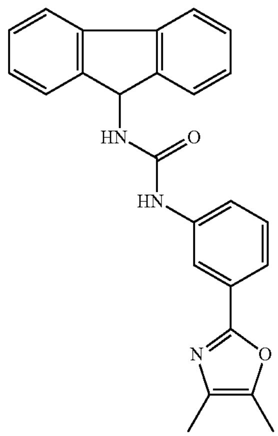 [SMILES: Cc1nc(-c2cccc(NC(=O)NC3c4ccccc4-c4ccccc43)c2)oc1C] | 1-[3-(4,5-dimethyl-1,3-oxazol-2-yl)phenyl]-3-(9H-fluoren-9-yl)urea | 396.1 |
| 66 | 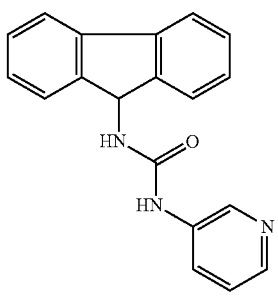 [SMILES: O=C(Nc1cccnc1)NC1c2ccccc2-c2ccccc21] | 1-(9H-fluoren-9-yl)-3-pyridin-3-ylurea | 302.1 |
| 67 | 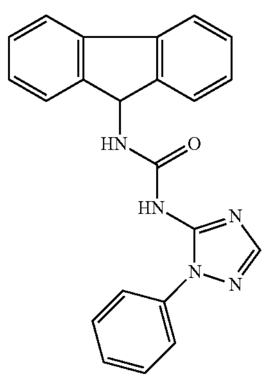 [SMILES: O=C(Nc1ncnn1-c1ccccc1)NC1c2ccccc2-c2ccccc21] | 1-(9H-fluoren-9-yl)-3-(1-phenyl-1H-1,2,4-triazol-5-yl)urea | 368.1 |
| 68 | 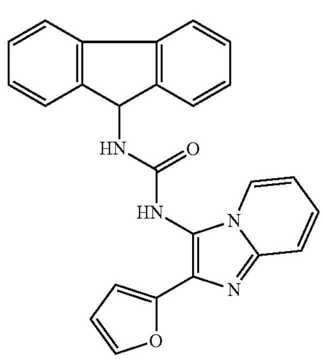 [SMILES: O=C(Nc1c(-c2ccco2)nc2ccccn12)NC1c2ccccc2-c2ccccc21] | 1-(9H-fluoren-9-yl)-3-(2-furan-2-ylimidazo[1,2-a]pyridin-3-yl)urea | 407.1 |

TABLE 1-continued
| Compound | Structure | IUPAC Name | Exact Mass [M + H]+ |
|---|---|---|---|
| 69 | 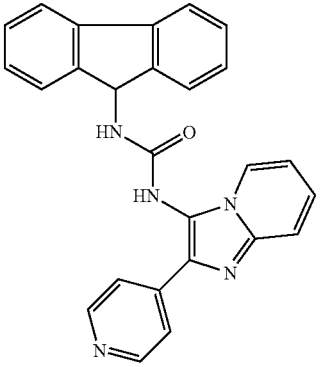 [SMILES: O=C(Nc1c(-c2ccncc2)nc2ccccn12)NC1c2ccccc2-c2ccccc21] | 1-(9H-fluoren-9-yl)-3-(2-pyridin-4-ylimidazo[1,2-a]pyridin-3-yl)urea | 418.1 |
| 70 | 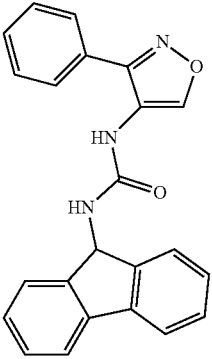 [SMILES: O=C(Nc1conc1-c1ccccc1)NC1c2ccccc2-c2ccccc21] | 1-(9H-fluoren-9-yl)-3-(3-phenylisoxazol-4-yl)urea | 368.4 |
| 71 | 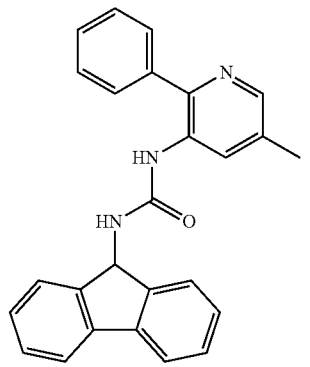 [SMILES: Cc1cnc(-c2ccccc2)c(NC(=O)NC2c3ccccc3-c3ccccc32)c1] | 1-(9H-fluoren-9-yl)-3-(5-methyl-2-phenylpyridin-3-yl)urea | 392.0 |
| 72 | 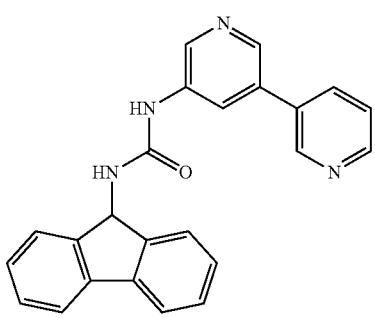 [SMILES: O=C(Nc1cncc(-c2cccnc2)c1)NC1c2ccccc2-c2ccccc21] | 1-(3,3'-bipyridin-5-yl)-3-(9H-fluoren-9-yl)urea | 379.426 |

TABLE 1-continued

| Compound | Structure | IUPAC Name | Exact Mass [M + H]+ |
|---|---|---|---|
| 73 | 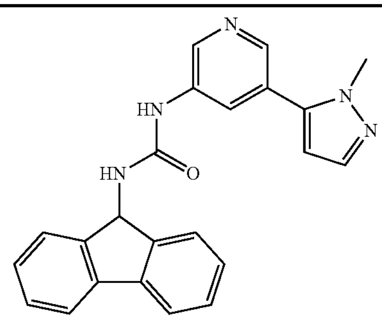 | 1-(9H-fluoren-9-yl)-3-[5-(1-methyl-1H-pyrazol-5-yl)pyridin-3-yl]urea | 382.43 |
| 74 | 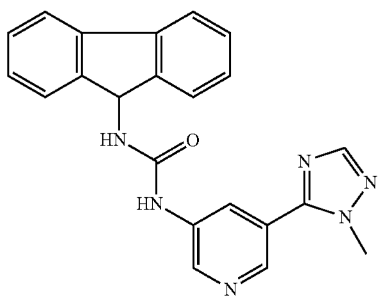 [SMILES: Cn1ncnc1-c1cncc(NC(=O)NC2c3ccccc3-c3ccccc32)c1] | 1-(9H-fluoren-9-yl)-3-[5-(1-methyl-1H-1,2,4-triazol-5-yl)pyridin-3-yl]urea | 383.1 |
| 75 | 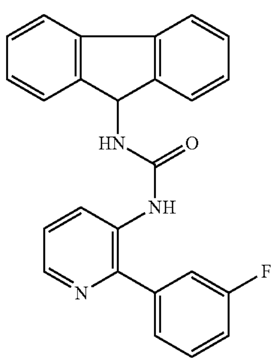 [SMILES: O=C(Nc1cccnc1-c1cccc(F)c1)NC1c2ccccc2-c2ccccc21] | 1-(9H-fluoren-9-yl)-3-[2-(3-fluorophenyl)pyridin-3-yl]urea | 396.1 |
| 76 | 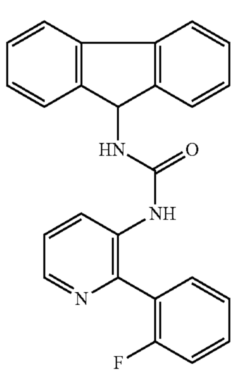 [SMILES: O=C(Nc1cccnc1-c1ccccc1F)NC1c2ccccc2-c2ccccc21] | 1-(9H-fluoren-9-yl)-3-[2-(2-fluorophenyl)pyridin-3-yl]urea | 396.1 |

TABLE 1-continued
| Compound | Structure | IUPAC Name | Exact Mass [M + H]+ |
|---|---|---|---|
| 77 | 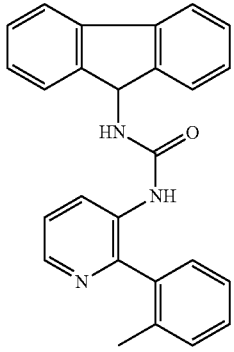 [SMILES: Cc1ccccc1-c1ncccc1NC(=O)NC1c2ccccc2-c2ccccc21] | 1-(9H-fluoren-9-yl)-3-[2-(2-methylphenyl)pyridin-3-yl]urea | 392.1 |
| 78 | 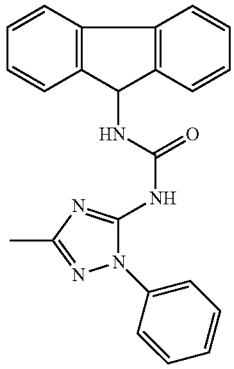 [SMILES: Cc1nc(NC(=O)NC2c3ccccc3-c3ccccc32)n(-c2ccccc2)n1] | 1-(9H-fluoren-9-yl)-3-(3-methyl-1-phenyl-1H-1,2,4-triazol-5-yl)urea | 382.16 |
| 79 | 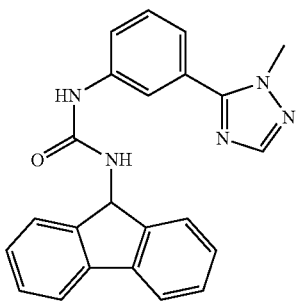 [SMILES: Cn1ncnc1-c1cccc(NC(=O)NC2c3ccccc3-c3ccccc32)c1] | 1-(9H-fluoren-9-yl)-3-[3-(1-methyl-1H-1,2,4-triazol-5-yl)phenyl]urea | 382.1 |
| 80 | 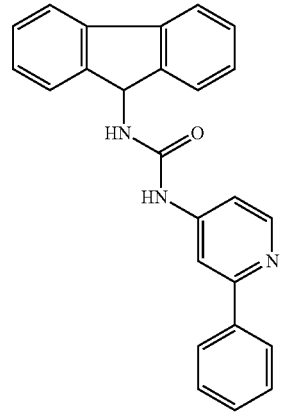 [SMILES: O=C(Nc1ccnc(-c2ccccc2)c1)NC1c2ccccc2-c2ccccc21] | 1-(9H-fluoren-9-yl)-3-(2-phenylpyridin-4-yl)urea | 378.15 |

TABLE 1-continued

| Compound | Structure | IUPAC Name | Exact Mass [M + H]+ |
|---|---|---|---|
| 81 | 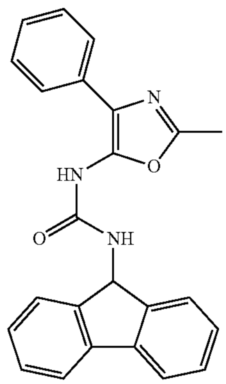 [SMILES: Cc1nc(-c2ccccc2)c(NC(=O)NC2c3ccccc3-c3ccccc32)o1] | 1-(9H-fluoren-9-yl)-3-(2-methyl-4-phenyl-1,3-oxazol-5-yl)urea | 382.427 |
| 82 | 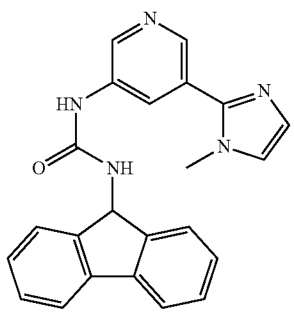 [SMILES: Cn1ccnc1-c1cncc(NC(=O)NC2c3ccccc3-c3ccccc32)c1] | 1-(9H-fluoren-9-yl)-3-[5-(1-methyl-1H-imidazol-2-yl)pyridin-3-yl]urea | 382.43 |
| 83 | 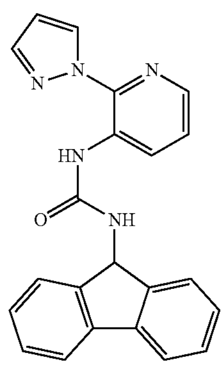 [SMILES: O=C(Nc1cccnc1-n1cccn1)NC1c2ccccc2-c2ccccc21] | 1-(9H-fluoren-9-yl)-3-[2-(1H-pyrazol-1-yl)pyridin-3-yl]urea | 368.0 |
| 84 | 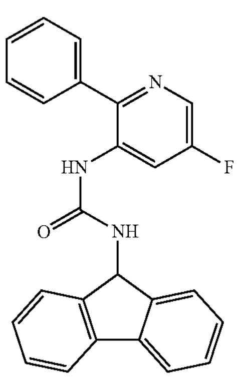 [SMILES: O=C(Nc1cc(F)cnc1-c1ccccc1)NC1c2ccccc2-c2ccccc21] | 1-(9H-fluoren-9-yl)-3-(5-fluoro-2-phenylpyridin-3-yl)urea | 396.1 |

TABLE 1-continued

| Compound | Structure | IUPAC Name | Exact Mass [M + H]+ |
|---|---|---|---|
| 85 | 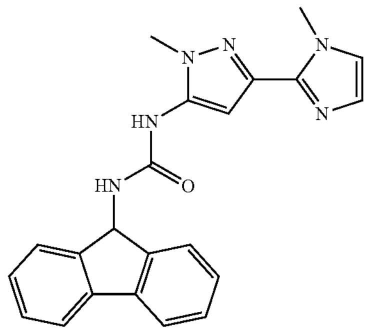 [SMILES: Cn1ccnc1-c1cc(NC(=O)NC2c3ccccc3-c3ccccc32)n(C)n1] | 1-(9H-fluoren-9-yl)-3-[1-methyl-3-(1-methyl-1H-imidazol-2-yl)-1H-pyrazol-5-yl]urea | 385.1 |
| 86 | | 1-[3-(4,5-dimethyl-4H-1,2,4-triazol-3-yl)phenyl]-3-(9H-fluoren-9-yl)urea | 396.1 | and pharmaceutically acceptable salts thereof.

The invention is also directed to methods of treating a patient (preferably a human) for diseases or disorders in which the TrkA receptor may be involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, by administering to the patient a therapeutically effective amount of a compound of the invention, or a pharmaceutically acceptable salt thereof.

The invention is also directed to the use of a compound of the invention for treating a disease or disorder in which the TrkA receptor may be involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, by administering to the patient a compound of the invention, or a pharmaceutically acceptable salt thereof.

The invention is also directed to medicaments or pharmaceutical compositions for the treatment of diseases or disorders in a patient (preferably a human) in which the TrkA receptor may be involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, which comprise a compound of the invention, or a pharmaceutically acceptable salt thereof, and a pharmaceutically acceptable carrier.

The invention is also directed to a method for the manufacture of a medicament or a pharmaceutical composition for treating diseases in which TrkA receptor may be involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA comprising combining a compound of the invention or a pharmaceutically acceptable salt thereof, with a pharmaceutically acceptable carrier.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

If and when $R^a$ is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyly, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl and N-oxides thereof.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

As used herein, unless otherwise specifically defined, substituted alkyl, substituted cycloalkyl, substituted aryl, substituted heteroaryl, and substituted heterocycle include moieties containing from 1 to 3 substituents in addition to the point of attachment to the rest of the compound. Preferably, such substituents are selected from the group which includes but is not limited to F, Cl, Br, $CF_3$, $NH_2$, $N(C_1\text{-}C_6$ alkyl$)_2$, $NO_2$, CN, $(C_1\text{-}C_6$ alkyl)O—, (aryl)O—, —OH, $(C_1\text{-}C_6$ alkyl)S(O)$_m$—, $(C_1\text{-}C_6$ alkyl)C(O)NH—, $H_2N$—C(NH)—, $(C_1\text{-}C_6$ alkyl)C(O)—, $(C_1\text{-}C_6$ alkyl)OC(O)—, $(C_1\text{-}C_6$ alkyl)OC(O)NH—, phenyl, pyridyl, imidazolyl, oxazolyl, isoxazolyl, thiazolyl, thienyl, furyl, isothiazolyl and $C_1\text{-}C_{20}$ alkyl.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae I, Ia, II, III, IV and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formulae formulae I, Ia, II, III, and IV. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formulae formulae I, Ia, II, III, and IV can be prepared without undue experimentation by conventional techniques well known to those skilled in the art or by processes analogous to those described in the Schemes and Examples herein using appropriate isotopically-enriched reagents and/or intermediates.

The term "substantially pure" means that the isolated material is at least 90% pure, and preferably 95% pure, and even more preferably 99% pure as assayed by analytical techniques known in the art.

As used herein, the term TrkA" refers to one of Trk's high affinity binding protein kinase receptors that are activated by Neurotrophins (NT), a group of soluble growth factors Nerve Growth Factor (NGF), Brain-Derived Neurotrophic Factor (BDNF) and Neurotrophin 3-5 (NT 3-5). The Trk's are made up of three family members TrkA, TrkB and TrkC that bind to and mediate the the signal transduction derived from the Neurotrophins. Inhibitors of the Trk/neutrophin pathway have been demonstrated to be highly effective in numerous pre-clinical animal models of pain. The compounds of the invention are modulators of the Trk receptors, particularly TrkA.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

The present invention is directed to the use of the compounds of formulae I, Ia, II, III, and IV disclosed herein as TrkA inhibitors in a patient or subject such as a mammal in need of such activity, comprising the administration of an effective amount of the compound. In addition to humans, a variety of other mammals can be treated according to the method of the present invention.

The compounds of the present invention may have utility in treating or ameliorating pain disorders (including pain associated with cancer, surgery, and bone fracture, acute pain, inflammatory pain and neuropathic pain). The compounds of formula formulae I, Ia, II, III, and IV also may beuseful for treating cancers including neuroblastoma, ovarian, pancreatic and colorectal cancer. Other conditions that may be treated by the compounds of the invention include inflammation and certain infectious diseases, interstitial cystitis, painful bladder syndrome, urinary incontinence, asthma, anorexia, atopic dermatitis, and psoriasis. Treament of demyelination and dysmyelination, by promoting myelination, neuronal survival, and oligodendrocyte differentiation via blocking Sp35-TrkA interaction may also be possible with the compounds of the present invention.

The compounds of formula formulae I, Ia, II, III, and IV may also be useful in the treatment of bone-related diseases (e.g., those involved in bone resorption). Examples of bone-related diseases include metastatic bone disease, treatment-induce bone loss, osteoporosis, rheumatoid arthritis, ankylosing spondylitis, Paget's disease, and periodontal disease. Another bone disorder or disease that can be treated with the compounds of the claimed invention is metastatic tumor-induced osteolysis. Cancers known to cause tumor induced osteolysis are hematological malignancies such as myeloma and lymphoma and solid tumors such as breast, prostate, lung, renal and thyroid.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally mammals such a human being, male or female, in whom Trk-A, Trk-B and/or Trk-C modulation is desired. Thus, an aspect of the present invention is a method of treating diseases with an inhibitor of Trk-A, Trk-B and/or Trk-C comprising administering to said mammal one or more compounds of formula formulae I, Ia, II, III, and IV, or a pharmaceutically acceptable salt thereof in an amount effective to treat or prevent said disorder. For purposes of this invention mammals include dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds include combinations with agents for the treatment of pain, for example steroids such as dexamethasone, cortisone, and fluticasone, non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib and valdecoxib; CB-2 agonists; VR-1 antagonists; bradykinin B 1 receptor antagonists; sodium channel blockers and antagonists; nitric oxide synthase (NOS) inhibitors (including iNOS and nNOS inhibitors); glycine site antagonists, including lacosamide; neuronal nicotinic agonists; NMDA antagonists; potassium channel openers; AMPA/kainate receptor antagonists; calcium channel blockers, such as ziconotide; GABA-A receptor IO modulators (e.g., a GABA-A receptor agonist); matrix metalloprotease (MMP) inhibitors; thrombolytic agents; chemotherapeutic agents, opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists; alpha agonists; neuronal nicotinic agonists; NMDA receptor agonists or antagonists; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

Another aspect of the present invention is directed to a pharmaceutical composition comprising a compound of formula formulae I, Ia, II, III, and IV, or a pharmaceutically acceptable salt thereof and a pharmaceutically acceptable diluent or carrier. Still another aspect of the present invention is directed to a compound of formula formulae I, Ia, II, III, and IV, or a pharmaceutically acceptable salt thereof, for use in the treatment of a condition treatable with an inhibitor of Trk-A, Trk-B and/or Trk-C, such as the disorders, conditions and/or diseases described herein. Still another aspect is directed to an invention where use of a compound of formula I or Ia or a pharmaceutically acceptable salt thereof in the treatment of pain, cancer, inflammation, neurodegenerative disease or *typanosoma cruzi* infection may be possible.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formula formulae I, Ia, II, III, or IV is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg.

This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials and the requisite intermediates are in some cases commercially available, or can be prepared according to literature procedures or as illustrated herein.

The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

During any of the synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1999. The protecting groups may be removed at a convenient sequent stage using methods known from the art.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

SCHEME I

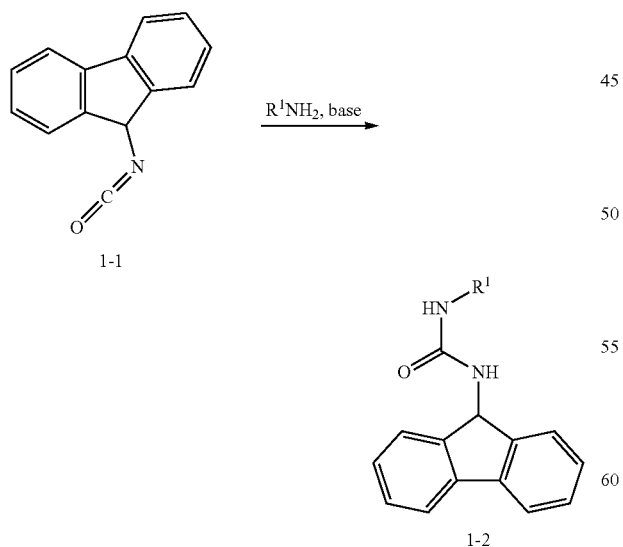

Reaction Scheme I illustrates the preparation of the compounds of the invention, starting with isocyanate 1-1. This material is reacted with the appropriate amines in the presence of base to yield ureas 1-2.

SCHEME II

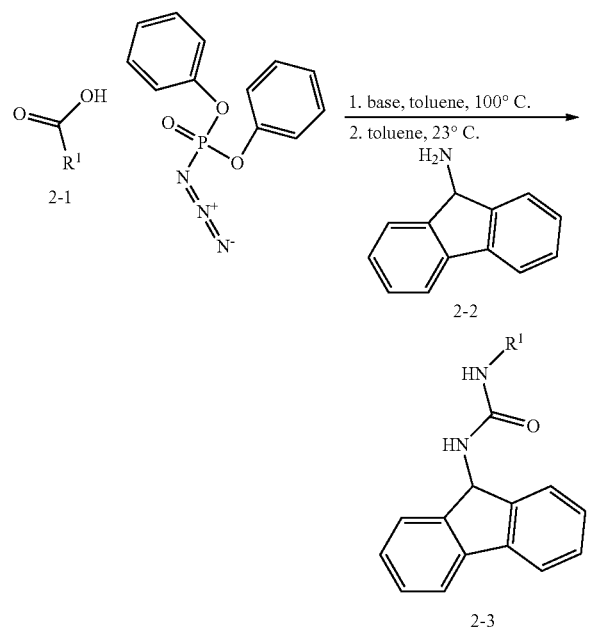

Reaction Scheme II illustrates the preparation of the compounds of the invention starting with the appropriate carboxylic acid 2-1. The material can be converted to the intermediate isocyanate using diphenylphosphorylazide and base in refluxing toluene, which is then treated with amine 2-2 to produce the desired urea 2-3.

SCHEME III

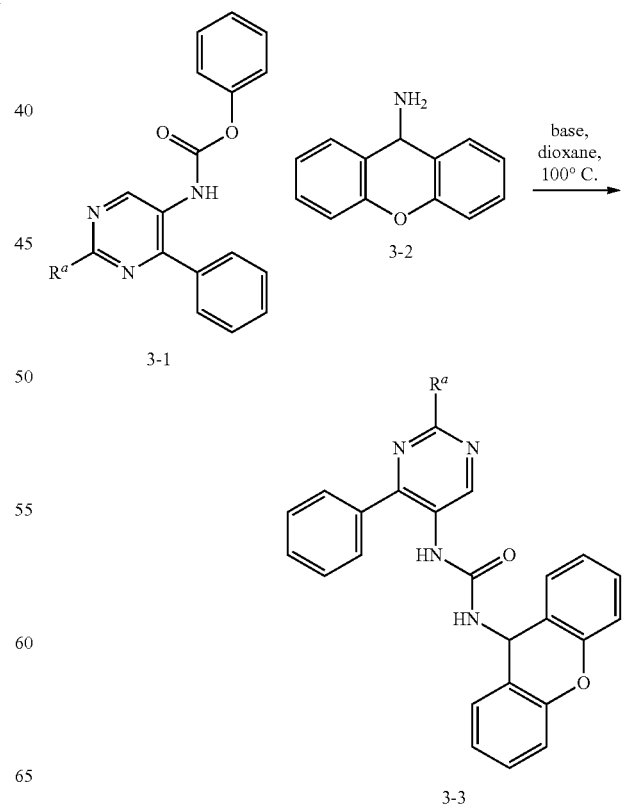

Reaction Scheme III illustrates the preparation of the compounds of the invention starting with phenyl carbamate 3-1. This material is reacted with amine 3-2 in the presence of base to yield urea 3-3.

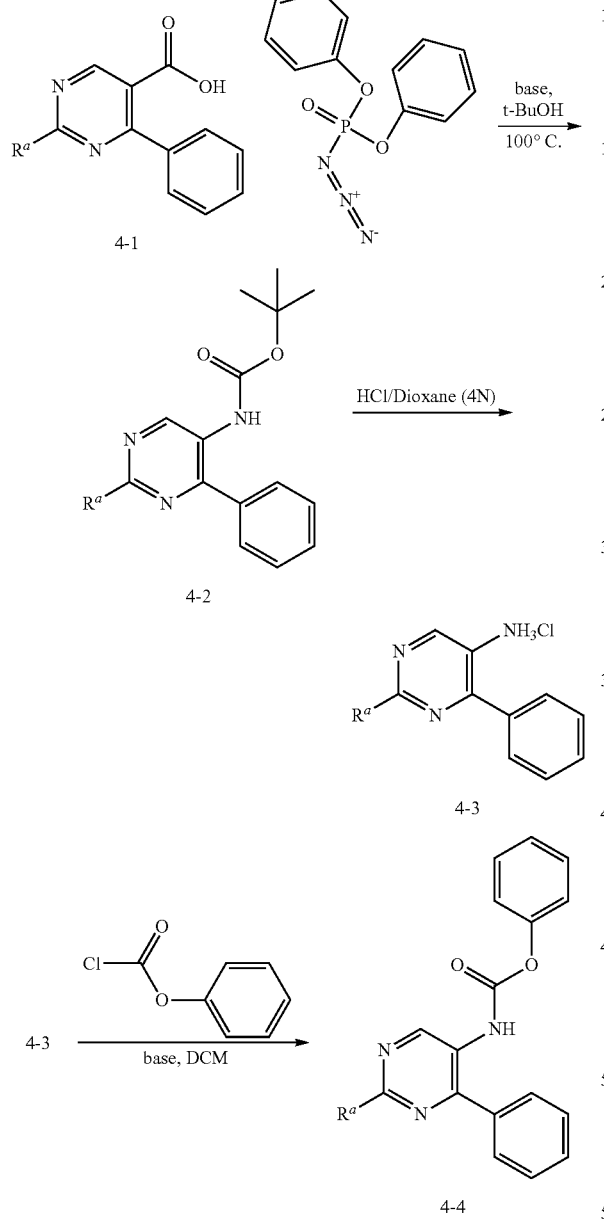

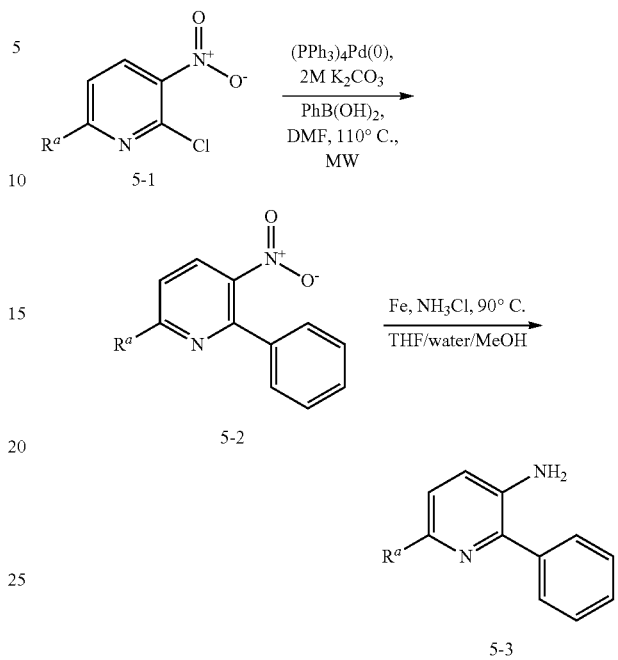

Reaction Scheme V illustrates the preparation of an intermediate such as pyridyl amine 5-3 from aryl halide 5-1. Displacement of the aryl chloride to yield the corresponding biaryl 5-2 is performed by cross coupling with a suitable arylboronic acid in the presence of a base/ligand/catalyst system such as $K_2CO_3$ and $Pd(PPh_3)_4$. The nitro group in 5-2 is reduced with iron to afford the amine 5-3.

Intermediate A1

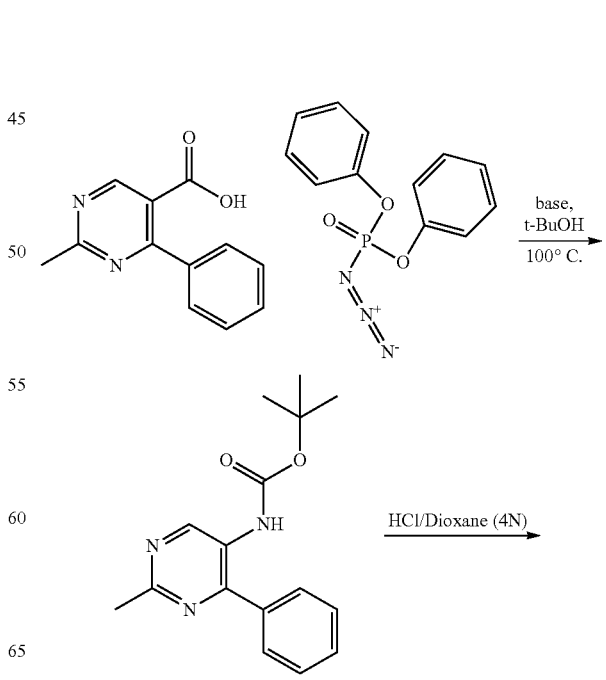

Reaction Scheme IV illustrates the preparation of intermediate phenyl carbamate 4-4 from carboxylic acid 4-1. Acid 4-1 undergoes Curtius Rearrangement via treatment with diphenylphosphorylazide in refluxing t-BuOH to yield the corresponding boc protected amine 4-2. Removal of the boc protecting group with HCl in dioxane provides amine 4-3 as the HCl salt. Phenyl carbamate 4-4 is formed by treatment of amine 4-3 with phenyl chloroformate in DCM in the presence of base.

-continued

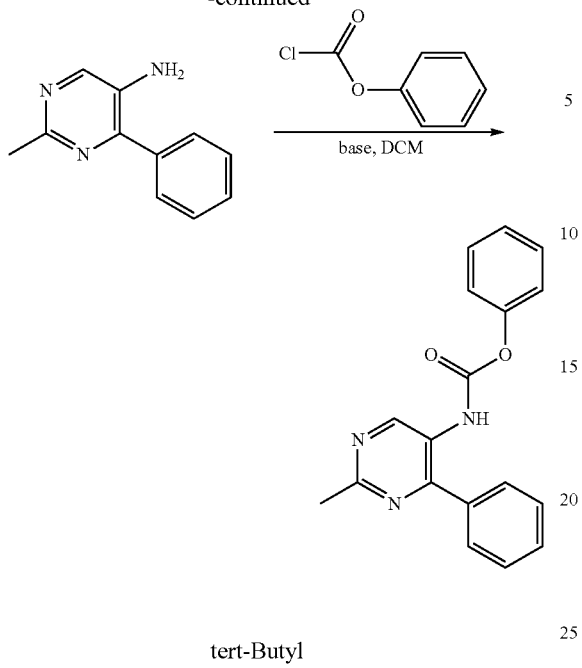

tert-Butyl (2-methyl-4-phenylpyrimidin-5-yl)carbamate

Step A: tert-Butyl (2-methyl-4-phenylpyrimidin-5-yl)carbamate

To a suspension of 2-methyl-4-phenyl-5-pyrimidinecarboxylic acid (5.00 g, 23.3 mmol) in tert-butanol (100 mL) was added diphenylphosphorylazide (6.05 mL, 28.0 mmol) and TEA (9.76 mL, 70.0 mmol). The resulting mixture was heated to reflux for 4 h, then concentrated. The residue was partitioned between saturated NaHCO$_3$ (100 mL) and DCM (4×100 mL). The combined organics were dried over Na$_2$SO$_4$, filtered, and concentrated in vacuo. The residue was purified directly by column chromatography on silica gel (ISCO 220 g—Teledyne ISCO), eluting with 0-50% EtOAc in hexanes to give the title compound. MS: m/z=286.1548 (M+H).

Step B: 2-Methyl-4-phenylpyrimidin-5-amine

A solution HCl in dioxane (4N, 42.1 ml, 168 mmol) and tert-butyl (2-methyl-4-phenylpyrimidin-5-yl)carbamate (4.80 g, 16.8 mmol) was stirred for 2 h. The reaction mixture was concentrated in vacuo to yield the title compound as the HCl salt. MS: m/z=186.1024 (M+H).

Step C: Phenyl (2-methyl-4-phenylpyrimidin-5-yl)carbamate

To a solution of 2-methyl-4-phenylpyrimidin-5-amine (590 mg, 2.66 mmol) and DIEA (1.16 mL, 6.65 mmol) in DCM (4 mL) was added dropwise a solution of phenyl chloroformate (0.334 mL, 2.66 mmol) in DCM (1 mL) at 25° C. After 3 h, additional phenyl chloroformate (0.05 mL, 0.40 mmol) was added and the reaction mixture was stirred for 2 h. The reaction mixture was poured into a mixture of water (10 mL) and saturated NaHCO$_3$ (5 mL), and the aqueous mixture was extracted with DCM (3×10 mL). The combined organics were dried over Na$_2$SO$_4$, filtered, and concentrated in vacuo to yield the title compound. MS: m/z=306.1 (M+H).

Intermediate A2

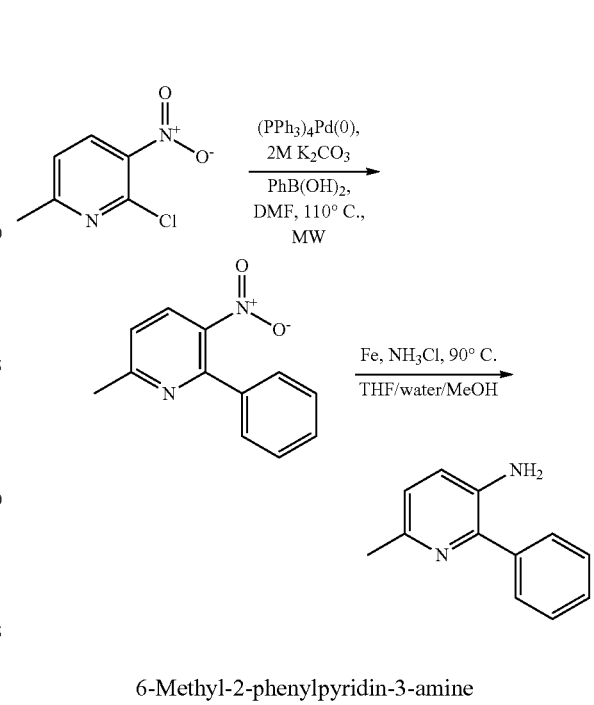

6-Methyl-2-phenylpyridin-3-amine

Step A: 6-Methyl-3-nitro-2-phenylpyridine

A deoxygenated mixture of 2-chloro-6-methyl-3-nitropyridine (500 mg, 2.90 mmol), phenylboronic acid (353 mg, 2.90 mmol), 2M potassium carbonate (2.90 mL, 5.79 mmol), and tetrakis(triphenylphosphine)palladium (0) (167 mg, 0.145 mmol) in DMF (6 mL) was heated in the microwave for 10 min at 110° C. The reaction mixture was partitioned between water (15 mL) and EtOAc (30 mL×2). The combined organic layers were washed with brine (10 mL), dried over anhydrous Na$_2$SO$_4$ and concentrated in vacuo. The residue was purified purified by column chromatography (ISCO 80 g silica, 0 to 30% EtOAc in hexanes) to give the title compound. MS: m/z=215.1 (M+H).

Step B: 6-methyl-2-phenylpyridin-3-amine

To a solution of 6-methyl-3-nitro-2-phenylpyridine (410 mg, 1.91 mmol) in a mixture of MeOH (10 mL), THF (10 mL) and water (5 mL) was added ammonia hydrochloride (563 mg, 10.5 mmol) and iron (534 mg, 9.57 mmol). The resulting mixture was stirred at 90° C. for 10 h. The resulting mixture was cooled to 23° C., filtered through celite, and the filter cake was washed with MeOH. The filtrate was concentrated and the residue was purified by column chromatography (ISCO 40 g column, 0 to 5% MeOH in DCM) to give the title compound. MS: m/z=185.1 (M+H).

COMPOUND 1

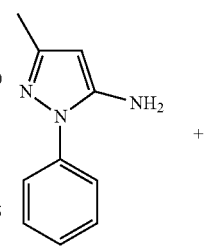

+

-continued

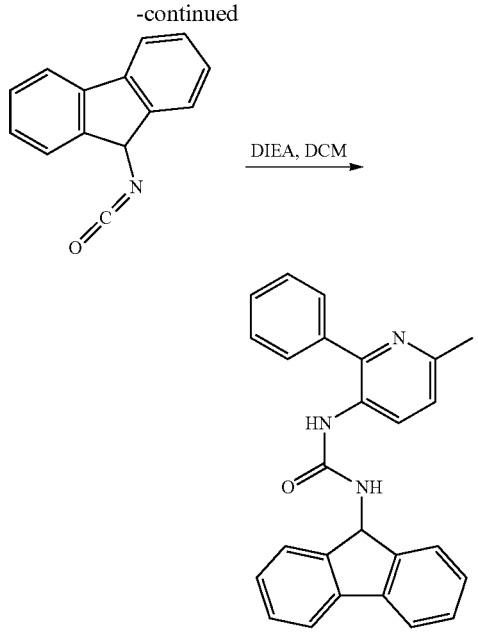

1-(9H-Fluoren-9-yl)-3-(6-methyl-2-phenylpyridin-3-yl)urea

A suspension of 9H-fluoren-9-yl isocyanate (20 mg, 0.097 mmol), 6-methyl-2-phenylpyridin-3-amine (18 mg, 0.097 mmol) and DIEA (0.034 mL, 0.19 mmol) in DCM (5 mL) was heated at reflux for 4 h. The reaction mixture was cooled to 23° C. and concentrated in vacuo. The residue was purified by prep-HPLC (5-95% acetonitrile+0.1% trifluoroacetic acid in water) to give the title compound. MS: m/z=392.2 (M+H). $^1$H NMR (500 MHz, DMSO): δ 8.28 (s, 1 H); 7.83 (d, J=7.5 Hz, 2 H); 7.63 (s, 1 H); 7.54 (d, J=7.4 Hz, 4 H); 7.46 (t, J=7.3 Hz, 2 H); 7.41 (t, J=7.3 Hz, 2 H); 7.33 (t, J=7.4 Hz, 2 H); 7.25 (d, J=8.1 Hz, 1 H); 7.21 (d, J=8.3 Hz, 1 H); 5.84 (d, J=7.8 Hz, 1 H); 2.54 (s, 3 H).

COMPOUND 2

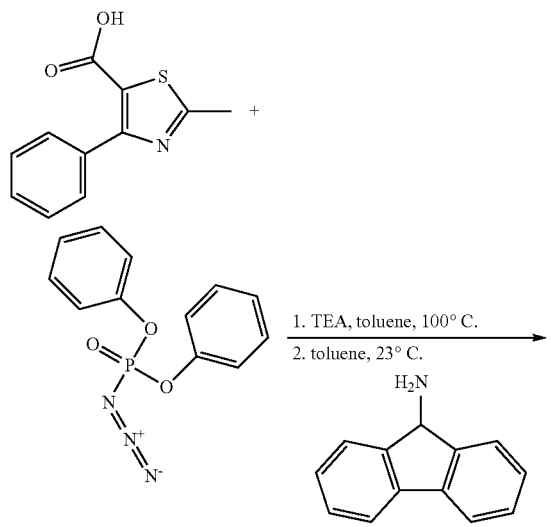

-continued

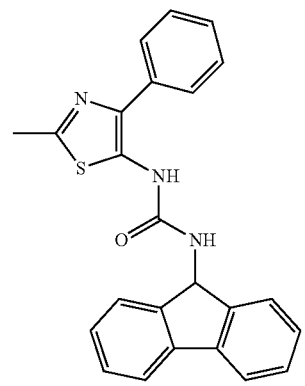

1-(9H-Fluoren-9-yl)-3-(2-methyl-4-phenylthiazol-5-yl)urea

To a solution of 2-methyl-4-phenyl-1,3-thiazole-5-carboxylic acid (20 mg, 0.091 mmol) and diphenylphosphorylazide (28 mg, 0.10 mmol) in toluene (1 mL) was added TEA (0.025 mL, 0.18 mmol). The resulting mixture was stirred at 23° C. for 1 h and then heated at reflux for 1 h. The reaction mixture was cooled to 23° C. and a solution of 9H-fluoren-9-amine (16 mg, 0.091 mmol) in toluene (1 mL) was added. The resulting mixture was stirred for 16 h at 23° C., then concentrated. The residue was purified by prep-HPLC (5-95% acetonitrile+0.1% trifluoroacetic acid in water) to give the title compound. MS: m/z=381.1 (M+H). $^1$H NMR (500 MHz, DMSO): δ 8.72 (s, 1 H); 7.86 (d, J=7.6 Hz, 2 H); 7.65 (d, J=7.7 Hz, 2 H); 7.59 (d, J=7.5 Hz, 2 H); 7.41-7.45 (m, 4 H); 7.29-7.37 (m, 4 H); 5.86 (d, J=8.0 Hz, 1 H); 2.58 (s, 3 H).

COMPOUND 3

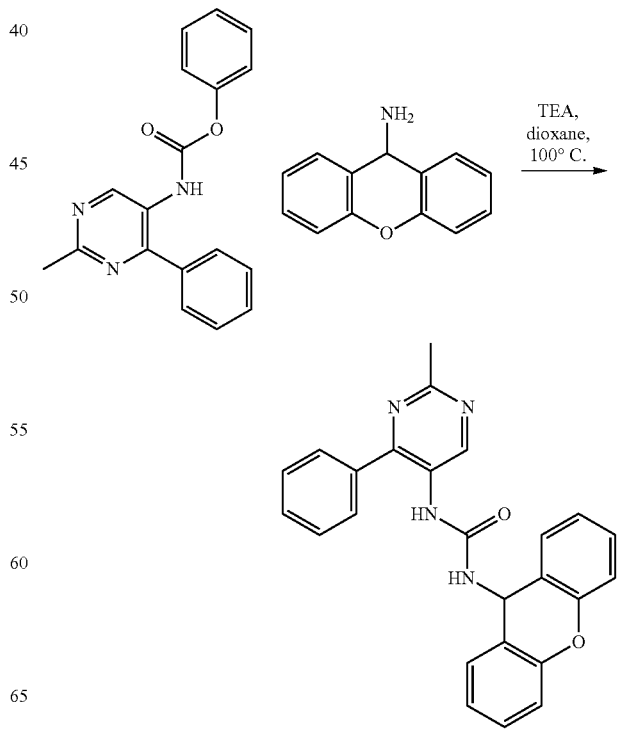

1-(2-Methyl-4-phenylpyrimidin-5-yl)-3-(9H-xanthen-9-yl)urea

A solution of 9H-xanthen-9-amine (11 mg, 0.056 mmol), triethylamine (10 uL, 0.075 mmol), and phenyl (2-methyl-4-phenylpyrimidin-5-yl)carbamate (11 mg, 0.037 mmol) in dioxane (1 mL) was heated at 100° C. for 22 h. The reaction mixture was cooled to 23° C. and concentrated in vacuo. The residue was purified by prep-HPLC (5-95% acetonitrile+ 0.1% trifluoroacetic acid in water) to give the title compound. MS: m/z=409.1 (M+H). $^1$H NMR (400 MHz, DMSO): δ 9.01 (s, 1 H); 7.75 (s, 1 H); 7.58-7.27 (m, 10 H); 7.11-7.09 (m, 4 H); 6.04 (d, J 5=9.3 Hz, 1 H); 2.56 (s, 3 H).

Biological Utility

TrkA functional activity was measured using a DiscoverX PathHunter assay. In this assay, U2OS cells are express TrkA receptor as a fusion with the weakly complementing fragment of B-galactosidase, which DiscoverX calls "Prolink (PK)"; additionally, Shc1 is fused with a larger fragment, which is called "Enzyme Acceptor (EA)". Activation of the TrkA receptor, upon NGF addition, results in the kinase domain being phosphorylated, resulting in subsequent recruitment of Shc1-EA protein. That recruitment results in an active B-galactosidase enzyme that is detected by addition of a chemiluminescent substrate.

All reagents were purchased from DiscoverX, except for the receptor agonists (NGF, BDNF, NT3) which were purchased from Peprotech. Cells were expanded and frozen into cryovials (TrkA p75 @passage 13, 1.5×10^7 cells/vial; TrkC p75 @passage 11, 1.5×10^7 cells/vial in InVitrogen Recovery Cell Freezing media), and stored in the vapor phase of liquid nitrogen, and thawed immediately before use. Thawed cells were added to a 384-well plate (BD Falcon 384-well white/clear, TC surface 120 uL assay plates (353963), 20 uL of 0.375e6 cells/mL=>7500 cells/well), and allowed to incubate overnight. Compound (10 mM starting dose: 202.5 nL compound yielding 0.81% DMSO final in total assay volume and starting doses 81 uM) was added the following morning and allowed to incubate on cells for 1 hour. Then, 5 uL EC80 of agonist (NGF for TrkA; BDNF for TrkB; NT3 for TrkC) was added and allowed to incubate for 3 hours at room temperature. DiscoverX PathHunter detection reagent is added (12 uL to plate and components diluted in parts as per kit instructions) and the plate is further incubated for 1 hour in the dark. The plate is read via luminescence on the Perkin Elmer Envision.

The percent inhibition was calculated for each compound concentration, and the $IC_{50}$ was determined using Equation 1 below.

$$\% \text{ Inhibition} = \left(\text{Max} + \frac{(\text{Max} - \text{Min})}{1 + \left(\frac{\text{Conc}}{IC_{50}}\right)^{\text{Hill}}}\right). \quad \text{Equation 1}$$

$IC_{50}$ values from the aforementioned assay for the compounds of this invention range between 5 nM to 10000 nM. $IC_{50}$ values for particular compounds of this invention are provided below in Table 2 below:

TABLE 2

| Compound | TrkA $IC_{50}$ (nM) |
| --- | --- |
| 1 | 69 |
| 2 | 140 |
| 3 | 61 |
| 4 | 82 |
| 5 | 230 |
| 6 | 35 |
| 7 | 44 |
| 8 | 190 |
| 9 | 530 |
| 10 | 210 |
| 11 | 27 |
| 12 | 280 |
| 13 | 2500 |
| 14 | 120 |
| 15 | 3000 |
| 16 | 69 |
| 17 | 200 |
| 18 | 850 |
| 19 | 69 |
| 20 | 190 |
| 21 | 28 |
| 22 | 310 |
| 23 | 330 |
| 24 | 550 |
| 25 | 1400 |
| 26 | 520 |
| 27 | 3200 |
| 28 | 150 |
| 29 | 480 |
| 30 | 170 |
| 31 | 960 |
| 32 | 1200 |
| 33 | 1700 |
| 34 | 1100 |
| 35 | 4000 |
| 36 | 3000 |
| 37 | 2300 |
| 38 | 3000 |
| 39 | 3000 |
| 40 | 200 |
| 41 | 83 |
| 42 | 110 |
| 43 | 130 |
| 44 | 410 |
| 45 | 1400 |
| 46 | 660 |
| 47 | 970 |
| 48 | 360 |
| 49 | 2800 |
| 50 | 880 |
| 51 | 3000 |
| 52 | 100 |
| 53 | 540 |
| 54 | 2800 |
| 55 | 390 |
| 56 | 410 |
| 57 | 1300 |
| 58 | 190 |
| 59 | 500 |
| 60 | 560 |
| 61 | 670 |
| 62 | 1300 |
| 63 | 96 |
| 64 | 330 |
| 65 | 310 |
| 66 | 3500 |
| 67 | 4800 |
| 68 | 970 |
| 69 | 770 |
| 70 | 2200 |
| 71 | 120 |
| 72 | 1400 |
| 73 | 2800 |
| 74 | 990 |
| 75 | 190 |
| 76 | 320 |
| 77 | 1200 |
| 78 | 520 |
| 79 | 73 |
| 80 | 670 |

TABLE 2-continued

| Compound | TrkA IC$_{50}$ (nM) |
|---|---|
| 81 | 3900 |
| 82 | 260 |
| 83 | 3000 |
| 84 | 47 |
| 85 | 100 |
| 86 | 250 |

The following abbreviations are used throughout the text:
Me: methyl
Et: ethyl
Bu: butyl
t-Bu: tert-butyl
Ar: aryl
Ph: phenyl
Bn: benzyl
Ac: acetyl
DMF.DMA N,N-dimethylformamide dimethyl acetal
DMSO dimethylsulfoxide
DMF N,N-dimethylformamide
DMEM: Dulbecco's Modified Eagle Medium (High Glucose)
THF: tetrahydrofuran
TEA: triethylamine
rt: room temperature
aq: aqueous
HPLC: high performance liquid chromatography
MS: mass spectrometry
RB: round bottom
CDI 1,1'-Carbonyldiimidazole
DCE 1,2-Dichlorethane
DCM Dichloromethane
HCl Hydrochloric acid
° C. degrees Celcius
BINAP 2,2'-bis(diphenylphosphino)-1,1'-binaphthalene
DMSO methyl sulfoxide
ATP adenosine triphosphate
DIEA Diisopropylethylamine While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula I:

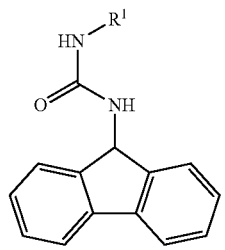

I and pharmaceutically acceptable salts thereof, wherein:
R represents hydrogen, or $C_{1-6}$ alkyl;
$R^1$ is selected from $C_{5-10}$ heterocycle, selected from the group consisting of pyrazolyl, pyridyl, imidazolyl, imidazopyridinyl, thiazolyl, isoxazolyl, triazolyl, oxazolyl, pyrimidinyl, pyrrolopyridinyl, and imidazothiazolyl, said heterocycle, optionally substituted with 1 to 3 groups of $R^a$;
$R^a$ represents —CN, —(CH$_2$)$_n$C$_{1-4}$haloalkyl, —C$_{1-6}$alkyl, —C$_{1-6}$alkenyl, —C$_{1-6}$alkynyl, —(CHR)$_n$C$_{6-10}$aryl, —(CHR)$_n$C$_{5-10}$ heterocycle, —C$_{3-10}$ cycloalkyl, —O—(CH$_2$)$_n$C$_{6-10}$ aryl, —O—C$_{5-10}$ heterocycle, —C(O)CF$_3$, —(CH$_2$)$_n$halo, —OR, —NRR, —NHC$_{6-10}$aryl, —SCF$_3$, —SO$_2$CF$_3$, —OC(F)$_2$Cl, —OC$_{1-4}$ haloalkyl, —C(O)NRR, —SO$_2$R, —SO$_2$NRR, —OC(F)$_2$C(F)$_3$, —S(O)$_2$CH(F)$_2$, —OC(F)$_2$CH(F)$_2$, —C(CH$_3$)$_2$C≡N, —COC$_{6-10}$ aryl, or —CO$_2$R, said cycloalkyl, alkyl, aryl and heterocycle optionally substituted with 1 to 3 groups of $R^b$, wherein the $C_{5-10}$ heterocycle is selected from the group consisting of pyrazolyl, pyridyl, imidazolyl, imidazopyridinyl, thiazolyl, isoxazolyl, triazolyl, oxazolyl, oxadiazolyl, thiadiazolyl, tetrazolyl, furanyl, pyrimidinyl, pyrrolopyridinyl, and imidazothiazolyl;
$R^b$ represents, —CN, —(CH$_2$)$_n$C$_{1-4}$haloalkyl, —OR, —C$_{1-6}$alkyl, —(CH$_2$)$_n$OR, —(CHR)$_n$C$_{6-10}$ aryl, —(CHR)$_n$C$_{5-10}$ heterocycle, —C$_{3-10}$ cycloalkyl, —(CH$_2$)$_n$halo, said aryl and heterocycle optionally substituted with 1 to 3 groups of C$_{1-6}$alkyl, or halo, wherein the $C_{5-10}$ heterocycle is selected from the group consisting of pyrazolyl, pyridyl, imidazolyl, imidazopyridinyl, thiazolyl, isoxazolyl, triazolyl, oxazolyl, oxadiazolyl, thiadiazolyl, tetrazolyl, furanyl, pyrimidinyl, pyrrolopyridinyl, and imidazothiazolyl, and
n represents 0-6.

2. The compound according to claim 1 wherein $R^a$ represents —CN, —CF$_3$, —OCF$_3$, —SCF$_3$, —C$_{1-6}$alkyl, —(CH$_2$)$_n$halo, —NRR, —C(O)NRR, pyrazolyl, furanyl, phenyl, pyridyl, tetrazolyl, oxazolyl, thiazolyl, pyrrolyl, triazolyl, imidazolyl, oxadiazolyl, thiadiazolyl, or —O(CH$_2$)$_n$phenyl, said pyrazolyl, furanyl, phenyl, pyridyl, tetrazolyl, oxazolyl, thiazolyl, pyrrolyl, triazolyl, imidazolyl, oxadiazolyl, thiadiazolyl, and —O(CH$_2$)$_n$phenyl optionally substituted with 1 to 3 groups of $R^b$.

3. The compound according to claim 1 of formula I represented by structural formula III:

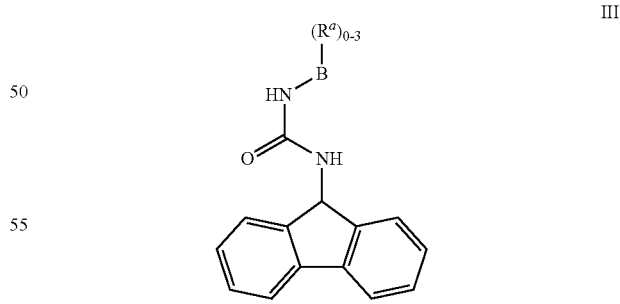

III or pharmaceutically acceptable salts there of wherein B is pyrazolyl or imidazolyl and $R^a$ is selected from the group consisting of —CN, —CF$_3$, —OCF$_3$, —SCF$_3$, —C$_{1-6}$alkyl, —(CH$_2$)$_n$halo, —NRR, —C(O)NRR, pyrazolyl, furanyl, phenyl, pyridyl, tetrazolyl, oxazolyl, thiazolyl, pyrrolyl, triazolyl, imidazolyl, oxadiazolyl, thiadiazolyl, and —O(CH$_2$)$_n$phenyl, said pyrazolyl, furanyl, phenyl, pyridyl, tetrazolyl, oxazolyl, thiazolyl, pyrrolyl, triazolyl, imidazolyl, oxadiazolyl, thiadiazolyl, and —O(CH$_2$)$_n$phenyl optionally substituted with 1 to 3 groups of R$^b$.

4. The compound according to claim 3 wherein B is pyrazolyl.

5. The compound according to claim 3 wherein B is imidazolyl.

6. The compound according to claim 1 of formula IV represented by structural formula IV:

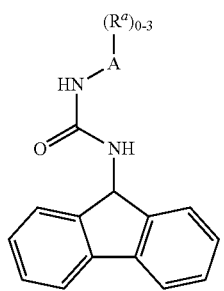

IV or pharmaceutically acceptable salts there of wherein A is pyridyl or pyrimidinyl and R$^a$ is selected from the group consisting of —CN, —CF$_3$, —OCF$_3$, —SCF$_3$, —C$_{1-6}$alkyl, —(CH$_2$)$_n$halo, —NRR, —C(O)NRR, pyrazolyl, furanyl, phenyl, pyridyl, tetrazolyl, oxazolyl, thiazolyl, pyrrolyl, triazolyl, imidazolyl, oxadiazolyl, thiadiazolyl, and —O(CH$_2$)$_n$phenyl, said pyrazolyl, furanyl, phenyl, pyridyl, tetrazolyl, oxazolyl, thiazolyl, pyrrolyl, triazolyl, imidazolyl, oxadiazolyl, thiadiazolyl, and —O(CH$_2$)$_n$phenyl, optionally substituted with 1 to 3 groups of R$^b$.

7. The compound according to claim 6 wherein A is pyridyl.

8. The compound according to claim 6 wherein A is pyrimidinyl.

9. A compound which is:
1-(9H-fluoren-9-yl)-3-(6-methyl-2-phenylpyridin-3-yl)urea;
1-(9H-fluoren-9-yl)-3-(2-methyl-4-phenyl-1,3-thiazol-5-yl)urea;
1-(9H-fluoren-9-yl)-3-(2-methyl-4-phenylpyrimidin-5-yl)urea;
1-(9H-fluoren-9-yl)-3-[2-(4-fluorophenyl)-6-methylpyridin-3-yl]urea;
1-(9H-fluoren-9-yl)-3-(6-phenylimidazo[2,1-b][1,3]thiazol-5-yl)urea;
1-(9H-fluoren-9-yl)-3-(3-methyl-1-phenyl-1H-pyrazol-5-yl)urea;
1-(9H-fluoren-9-yl)-3-(5-methyl-3-phenylisoxazol-4-yl)urea;
1-(9H-fluoren-9-yl)-3-(1-methyl-4-phenyl-1H-pyrazol-5-yl)urea;
1-(1,3-dimethyl-4-phenyl-1H-pyrazol-5-yl)-3-(9H-fluoren-9-yl)urea;
1-(9H-fluoren-9-yl)-3-(2-phenylpyridin-3-yl)urea;
1-(9H-fluoren-9-yl)-3-(4-phenylpyridin-3-yl)urea;
1-(9H-fluoren-9-yl)-3-(6-methylpyridin-3-yl)urea;
1-(9H-fluoren-9-yl)-3-(1-phenyl-1H-pyrazol-5-yl)urea;
1-(1,3-diphenyl-1H-pyrazol-5-yl)-3-(9H-fluoren-9-yl)urea;
1-(3-tert-butyl-1-phenyl-1H-pyrazol-5-yl)-3-(9H-fluoren-9-yl)urea;
1-(9H-fluoren-9-yl)-3-[3-(2-methylpropyl)-1-phenyl-1H-pyrazol-5-yl]urea;
1-[3-tert-butyl-1-(2-methylphenyl)-1H-pyrazol-5-yl]-3-(9H-fluoren-9-yl)urea;
1-(3-cyclopropyl-1-phenyl-1H-pyrazol-5-yl)-3-(9H-fluoren-9-yl)urea;
1-[3-tert-butyl-1-(4-fluorophenyl)-1H-pyrazol-5-yl]-3-(9H-fluoren-9-yl)urea;
1-(9H-fluoren-9-yl)-3-(2-phenylimidazo[1,2-a]pyridin-3-yl)urea;
1-(9H-fluoren-9-yl)-3-(1-methyl-4-phenyl-1H-imidazol-5-yl)urea;
1-[4-cyano-1-(4-fluorophenyl)-3-methyl-1H-pyrazol-5-yl]-3-(9H-fluoren-9-yl)urea;
1-(9H-fluoren-9-yl)-3-[3-(4-methoxyphenyl)-1-phenyl-1H-pyrazol-5-yl]urea;
1-(9H-fluoren-9-yl)-3-[2-(methylamino)pyridin-3-yl]urea;
1-(9H-fluoren-9-yl)-3-(2-fluoro-6-methylpyridin-3-yl)urea;
1-(9H-fluoren-9-yl)-3-[4-(4-fluorophenyl)-2-methylpyrimidin-5-yl]urea;
1-(9H-fluoren-9-yl)-3-[4-(4-fluorophenyl)-6-methylpyridin-3-yl]urea;
1-(9H-fluoren-9-yl)-3-(4-phenylpyrimidin-5-yl)urea;
1-(9H-fluoren-9-yl)-3-(3-methyl-1-pyridin-2-yl-1H-pyrazol-5-yl)urea;
1-(2-cyclohexylpyridin-3-yl)-3-(9H-fluoren-9-yl)urea;
1-(9H-fluoren-9-yl)-3-[1-(4-fluorophenyl)-3-methyl-1H-pyrazol-5-yl]urea;
1-(2,4'-bipyridin-3-yl)-3-(9H-fluoren-9-yl)urea;
1-(2,3'-bipyridin-3-yl)-3-(9H-fluoren-9-yl)urea;
1-(9H-fluoren-9-yl)-3-[2-(4-fluorophenyl)pyridin-3-yl]urea;
1-(9H-fluoren-9-yl)-3-(2'-fluoro-2,4'-bipyridin-3-yl)urea;
1-(9H-fluoren-9-yl)-3-(2-furan-2-ylpyridin-3-yl)urea;
1-(9H-fluoren-9-yl)-3-(1-methyl-3-phenyl-1H-pyrazol-5-yl)urea;
1-(1,2-dimethyl-4-phenyl-1H-imidazol-5-yl)-3-(9H-fluoren-9-yl)urea;
1-(9H-fluoren-9-yl)-3-(2-methyl-4-phenyl-1H-imidazol-5-yl)urea;
1-(9H-fluoren-9-yl)-3-pyridin-3-ylurea;
1-(9H-fluoren-9-yl)-3-(1-phenyl-1H-1,2,4-triazol-5-yl)urea;
1-(9H-fluoren-9-yl)-3-(2-furan-2-ylimidazo[1,2-a]pyridin-3-yl)urea;
1-(9H-fluoren-9-yl)-3-(2-pyridin-4-ylimidazo[1,2-a]pyridin-3-yl)urea;
1-(9H-fluoren-9-yl)-3-(3-phenylisoxazol-4-yl)urea;
1-(9H-fluoren-9-yl)-3-(5-methyl-2-phenylpyridin-3-yl)urea;
1-(3,3'-bipyridin-5-yl)-3-(9H-fluoren-9-yl)urea;
1-(9H-fluoren-9-yl)-3-[5-(1-methyl-1H-pyrazol-5-yl)pyridin-3-yl]urea;
1-(9H-fluoren-9-yl)-3-[5-(1-methyl-1H-1,2,4-triazol-5-yl)pyridin-3- yl]urea;
1-(9H-fluoren-9-yl)-3-[2-(3-fluorophenyl)pyridin-3-yl]urea;
1-(9H-fluoren-9-yl)-3-[2-(2-fluorophenyl)pyridin-3-yl]urea;
1-(9H-fluoren-9-yl)-3-[2-(2-methylphenyl)pyridin-3-yl]urea;
1-(9H-fluoren-9-yl)-3-(3-methyl-1-phenyl-1H-1,2,4-triazol-5-yl)urea;
1-(9H-fluoren-9-yl)-3-(2-phenylpyridin-4-yl)urea;

1-(9H-fluoren-9-yl)-3-(2-methyl-4-phenyl-1,3-oxazol-5-yl)urea,
1-(9H-fluoren-9-yl)-3-[5-(1-methyl-1H-imidazol-2-yl)pyridin-3-yl]urea;
1-(9H-fluoren-9-yl)-3-[2-(1H-pyrazol-1-yl)pyridin-3-yl]urea;
1-(9H-fluoren-9-yl)-3-(5-fluoro-2-phenylpyridin-3-yl)urea;
1-(9H-fluoren-9-yl)-3-[1-methyl-3-(1-methyl-1H-imidazol-2-yl)-1H-pyrazol-5-yl]urea;
and pharmaceutically acceptable salts thereof.

10. A pharmaceutical composition comprising a therapeutically effective amount of a compound of claim 1 or a pharmaceutically acceptable salt thereof,
and a pharmaceutically acceptable carrier.

\* \* \* \* \*